United States Patent [19]

Plischke et al.

[11] Patent Number: 5,977,014
[45] Date of Patent: Nov. 2, 1999

[54] ABSORBENT COMPOSITE STRUCTURE FORMED OF A SUBSTRATE AND CROSS-LINKABLE HYDROGEL POLYMER PARTICLES

[75] Inventors: Manfred Plischke, Steinbach/Ts.; Mattias Schmidt, Idstein, both of Germany; Ebrahim Rezai, Motoyama-Kita, Japan

[73] Assignee: The Procter & Gamble Company, Cincinnati, Ohio

[21] Appl. No.: 08/809,557

[22] PCT Filed: Aug. 21, 1995

[86] PCT No.: PCT/US95/10653

§ 371 Date: Mar. 10, 1997

§ 102(e) Date: Mar. 10, 1997

[87] PCT Pub. No.: WO96/07476

PCT Pub. Date: Mar. 14, 1996

Related U.S. Application Data

[63] Continuation-in-part of application No. 08/550,181, Oct. 30, 1995, Pat. No. 5,713,881, which is a continuation of application No. 08/142,259, Oct. 22, 1993, abandoned.

[30] Foreign Application Priority Data

Sep. 9, 1994 [EP] European Pat. Off. .............. 94114176

[51] Int. Cl.⁶ ..................................... A61F 13/15
[52] U.S. Cl. ........................... 502/401; 604/368; 604/378
[58] Field of Search .................................. 604/368, 369, 604/378; 502/401

[56] References Cited

U.S. PATENT DOCUMENTS

| | | | |
|---|---|---|---|
| 3,669,103 | 6/1972 | Harper et al. | 128/156 |
| 3,670,731 | 6/1972 | Harmon | 260/248 |
| 3,699,103 | 10/1972 | Harper et al. | 260/210 |
| 4,076,673 | 2/1978 | Burkholder, Jr. | 260/29.2 |
| 4,410,571 | 10/1983 | Korpman | 427/385.5 |
| 4,861,539 | 8/1989 | Allen et al. | 264/204 |
| 4,970,267 | 11/1990 | Bailey et al. | 525/344 |
| 5,013,309 | 5/1991 | Baigas, Jr. et al. | 604/368 |
| 5,102,597 | 4/1992 | Roe et al. | 264/126 |
| 5,124,188 | 6/1992 | Roe et al. | 428/72 |
| 5,164,459 | 11/1992 | Kimura et al. | 525/384 |
| 5,180,622 | 1/1993 | Berg et al. | 428/283 |
| 5,314,420 | 5/1994 | Smith et al. | 604/358 |
| 5,324,561 | 6/1994 | Rezai et al. | 428/72 |
| 5,376,503 | 12/1994 | Audett et al. | 430/270 |
| 5,536,264 | 7/1996 | Hsueh et al. | 604/368 |
| 5,713,881 | 2/1998 | Rezai et al. | 604/368 |

FOREIGN PATENT DOCUMENTS

| | | | |
|---|---|---|---|
| 0 160 572 A2 | 11/1985 | European Pat. Off. | A61F 13/18 |
| 0 273 141 B1 | 7/1988 | European Pat. Off. | A61F 15/00 |
| 0 443 627 A2 | 8/1991 | European Pat. Off. | A61F 13/46 |
| 0 631768 A1 | 1/1995 | European Pat. Off. | A61F 13/15 |
| 0 640 330 A1 | 3/1995 | European Pat. Off. | A61F 13/46 |
| 0 695 541 A1 | 2/1996 | European Pat. Off. | A61F 13/15 |
| 91/09582 | 7/1991 | WIPO | A61F 13/46 |
| 93/22998 | 11/1993 | WIPO | A61F 13/15 |
| 94/01069 | 1/1994 | WIPO | A61F 13/15 |
| 94/02092 | 2/1994 | WIPO | A61F 13/15 |

*Primary Examiner*—Steven Bos
*Assistant Examiner*—Stuart L. Hendrickson
*Attorney, Agent, or Firm*—Kevin D. Hogg; Carl J. Roof; Jacobus C. Rasser

[57] ABSTRACT

An absorbent composite structure suitable for absorbing aqueous body fluids is provided which includes a substrate having two surfaces, a plurality of hydrogel-forming polymer particles and a chemical cross-linking agent capable of bonding to both the substrate and the hydrogel-forming particles. In at least a substantial portion of the structure, the majority of the hydrogel-forming polymer particles are connected by the chemical cross-linking agent directly to at least one of the substrate surfaces. The absorbent composite structure can be incorporated into an absorbent article. A method of making the absorbent composite structure is also disclosed.

23 Claims, 7 Drawing Sheets

5,977,014

ABSORBENT COMPOSITE STRUCTURE FORMED OF A SUBSTRATE AND CROSS-LINKABLE HYDROGEL POLYMER PARTICLES

This is a continuation-in-part of application Ser. No. 08/550,181, filed on Oct. 30, 1995, now U.S. Pat. No. 5,713,881, which is a continuation of application Ser. No. 08/142,259 filed on Oct. 22, 1993, now abandoned.

FIELD OF THE INVENTION

The invention relates to an absorbent composite structure comprising a substrate having an upper and a lower surface and a plurality of hydrogel-forming polymer particles chemically bonded to at least one surface of the substrate, wherein the polymer particles each comprise a plurality of cross-linked molecules. The invention also relates to an absorbent article comprising such an absorbent composite structure and to a method of making such a structure.

BACKGROUND OF THE INVENTION

Particulate, absorbent, polymeric compositions are capable of absorbing large quantities of liquids such as water and body exudates (e.g., urine) and are further capable of retaining such absorbed liquids under moderate pressures. The absorption characteristics of such polymeric compositions make them especially useful for incorporation into absorbent articles such as diapers. See, for example, U.S. Pat. No. 3,669,103 (Harper et al), issued Jun. 13, 1972, and U.S. Pat. No. 3,670,731 (Harmon), issued Jun. 20, 1972, that disclose the use of particulate, absorbent, polymeric compositions (often referred to as "hydrogels", "superabsorbents", or "hydrocolloid materials") in absorbent articles.

Conventional particulate, absorbent, polymeric compositions, however, have the limitation that the particles are not immobilised and are free to migrate during processing and/or use. Migration of the particles can lead to material handling losses during manufacturing as well as non-homogeneous incorporation of the particles into structures in which the particles are being used. Especially when the absorbent polymer particles are incorporated in a fibrous matrix at high concentrations, the particles may sift out of the matrix of may become inhomogeneously distributed in an uncontrolled manner, as for instance described in European application number 94111955.4 (Bogdanski et. al.) Another significant problem occurs when these particulate materials migrate during or after swelling in use. Such mobility leads to high resistance to liquid flow through the material due to the lack of stable interparticle capillary or liquid transport channels. This phenomenon is one form of what is commonly referred to as "gel blocking."

One attempt to overcome the performance limitations associated with absorbent particle mobility during use in absorbent articles is incorporation of the particulate, absorbent, polymeric compositions into tissue laminates, i.e. layered absorbent structures. By encapsulating the particles between tissue layers, and affixation of the particles by water bonding or glue bonding, the overall particle mobility within an absorbent structure is diminished. However, upon liquid contact, the particles within the laminate are often free to move relative to each other resulting in the breakdown of any pre-existent interparticle capillary channels.

Another attempted solution is to immobilise the particulate, absorbent, polymeric compositions by the addition of large quantities of liquid polyhydroxy compounds that act as an adhesive to hold the particles together or attach the particles to a substrate. See, for example, U.S. Pat. No. 4,410,571 (Korpman), issued Oct. 18, 1983. While this approach does limit migration before and, to some extent, during swelling, the particles eventually become detached from each other or from the substrate in the presence of excess liquid, resulting again in the breakdown of any pre-existing capillary channels between the particles.

Another attempted solution to overcome the problem of absorbent particle mobility is to produce a hydrogel-forming film by extrusion of a solution of a linear absorbent polymer and subsequently crosslinking it. See, for example, U.S. Pat. No. 4,861,539 (Allen at al), issued Aug. 29, 1989 (crosslinked with a polyhydroxy compound such as a glycol or glycerol); and U.S. Pat. No. 4,076,673 (Burkholder), issued Feb. 28, 1978 (crosslinked with polyamine-polyamide epichlorohydrin adducts such as Kymene®). While these hydrogel-forming films may absorb significant quantities of liquids, they have limited liquid transport properties because they are essentially non-porous, i.e. lack internal capillary channels. Indeed, due to the lack of internal capillary channels, these hydrogel-forming films are especially prone to gel blocking.

A more recent solution proposed to overcome the problem of absorbent particle mobility is to form these particles into aggregate macrostructures, typically as sheets of bonded absorbent particles. See U.S. Pat. No. 5,102,597 (Roe et al), issued Apr. 7, 1992. These aggregate macrostructures are prepared by initially mixing the absorbent particles with a solution of a nonionic crosslinking agent, water and a hydrophilic organic solvent such as isopropanol. These nonionic crosslinking agents include polyhydric alcohols (e.g., glycerol), polyaziridine compounds (e.g., 2,2-bishydroxymethyl butanoltris[3-(1-aziridine) propionate]), haloepoxy compounds (e.g., epicholorhydrin), polyaldehyde compounds (e.g., glutaraldehyde), polyamine compounds (e.g., ethylene amine), and polyisocyanate compounds (e.g., 2,4-toluene diisocyanate), preferably glycerol. See Column 11, lines 22–54, of U.S. Pat. No. 5,102,597.

It has been described in U.S. Pat. No. 5,102,597 that the hydrogel-forming polymeric precursor particles may be brought into mutual contact by first depositing the particles on a substrate and subsequently effecting inter-particle crosslinking of the contiguous particles.

According to U.S. Pat. No. 5,124,188, reinforcement structures such as fibers, webs or scrims may be embedded into the macrostructures of crosslinked particles, to provide structural integrity. Embedding the fibers or webs into the macrostructure of crosslinked particles is effected by mixing the fibers with the solution containing the inter-particle crosslinking agent or by mixing the fibers with the particles prior to inter-particle cross-linking. Kneading the fibers into the interparticle crosslinking agent/precursor particle mix is preferred.

In U.S. Pat. No. 5,180,622 (Berg), the formation of an interparticle crosslinked aggregate is described, wherein the aggregate is joined to a carrier, which may be comprised of cellulosic fibers or which may be formed by a web. Joining the aggregate and the carrier is generally described as being effected via physical or chemical bonding using adhesives or chemicals that react to adhere the macrostructure, or inter-particle crosslinked aggregate, to the carrier.

The known formation of composites of combined inter-particle crosslinked aggregates and reinforcing webs is relatively complex, and results in structures which comprise a relatively large weight of hydrogel-forming polymeric particles relative to the weight of the substrate or carrier. Hence the known composites are less suitable for absorbent products in which less absorbency is required, such as for instance pantiliners.

Also, joining of the interparticle crosslinked aggregate to a web, will lead to some degree of loss of flexibility of the combined substrate and aggregate. Composites of good flexibility may be obtained, although this requires addition of for instance a plasticiser to the interparticle crosslinked aggregates. However, it has been found that known interparticle crosslinked aggregates may lose water when stored for a larger period of time in a dry environment. This may then cause the aggregates to become stiff or brittle.

Finally, the known interparticle crosslinked aggregates are relatively fluid stable as they isotropically expand upon being wetted. However, the inter-particle crosslinked aggregates may form a resistance to vertical transmission of liquid through the absorbent structure, which in multilayer absorbent products as described in European application no. 93305150.0 and no 93309614.1 may lead to reduced acquisition or fluid uptake rates.

In EP-B-0 273 141 it has been described to adhere hydrogel-forming polymeric particles to fibers to form absorbent flocks. The particles are attached to the fibers by adhesive attachment or by mixing fibers and monomers followed by polymerisation to form the absorbent polymer in which the fibers are embedded. A preferred way of attaching fibers and particles is by dissolving the polymeric particles in water, mixing the fibers into the solution, drying the solution to solidify the polymeric material, and grinding the polymeric material-fiber composite to form flocks of the desired size.

The absorbent flocks have as a disadvantage that adhesive attachment of polymeric particles to the fibers may negatively impact on the absorptive properties of the particles. Furthermore, an absorbent product formed of a multiplicity of flocks will not isotropically swell upon being wetted and hence have a tendency to exhibit gel blocking.

It is an object of the present invention to form an absorbent composite structure comprising hydrogel-forming polymeric particles connected to a substrate which do not become detached from the substrate upon being wetted.

It is a further object of the invention to provide an absorbent composite structure in which the hydrogel-forming polymeric particles have a reduced tendency to exhibit gel blocking.

It is again a further object of the invention to provide an absorbent structure which comprises a relatively low basis weight of hydrogel-forming polymeric particles.

It another object of the invention to provide an absorbent composite structure which is flexible and which has relatively little resistance to vertical transmission of liquids.

SUMMARY OF THE INVENTION

An absorbent composite structure according to the present invention is characterised in that the substrate and the hydrogel-forming polymer particles are connected by a crosslinking agent capable of crosslinking the molecules of the particles, wherein the degree of inter particle crosslinking between the particles is sufficiently low that no inter-particle crosslinked macrostructures are formed of circumscribed dry volume larger than 10 mm$^3$.

Upon bonding the hydrogel particles to the substrate, care is taken that no coherent, self-supporting macrostructure is formed, either prior to contacting the particles with the substrate or upon interparticle crosslinking during the bonding of the particles to the substrate by the crosslinking agent. With a self-supporting macroscopic structure, is meant an aggregate of inter-particle crosslinked hydrogel-forming particles mutually bonded by interparticle crosslink bonds having a circumscribed dry volume of at least 10 mm$^3$.

This is achieved for instance by maintaining a sufficient distance between adjacent hydrogel-forming particles by application of relatively low basis weights of absorbent particles to the substrate, followed by bonding the particles to the substrate. A basis weight below 100 g/m$^2$ will for typical hydrogel-forming particles of mass median particle size of about 400 micro meters prevent interparticle crosslinked bonds from forming upon attachment of the absorbent particles to the substrate by crosslinking. Preferably, the basis weight of the hydrogel-forming particles is sufficiently low that in a pre-determined area of the substrate at least 50% of the particles do not contact another particle.

Another way of preventing the formation of interparticle crosslinked macrostructures, is by preventing the crosslinking agent, that bonds the particles to the substrate, from migrating into the space between adjacent particles, for instance by applying the crosslinking agent only to the substrate-particle interface.

The crosslink bonds formed between the hydrogel-forming particles and the substrate do not negatively affect the absorbent properties of the hydrogel-forming particles, as is the case for instance with adhesive bonding.

The crosslink bonds between the hydrogel-forming particles and the substrate are relatively little affected by wetting. As the particles swell when absorbing liquid, they remain bonded to the substrate. The relative position between the bonded hydrogel-forming particles is hereby maintained and gel blocking due to contact of neighbouring swollen particles is reduced.

Simultaneously with bonding of the hydrogel-forming particles to the substrate, a surface cross-linking of the individual particles can take place to modify the surface properties of each hydrogel-forming particle. An increased degree of surface crosslinking of the particles will lead to an increased absorption against pressure of the particles, and will help to maintain good permeability of the particle-substrate composite.

By attaching the hydrogel-forming particles to the substrate in an individual manner, rather than in the form of a macroscopic structure, comprising an interparticle crosslinked aggregate, the total absorbent capacity of the composite absorbent structure according to the invention can be reduced, the liquid transmission can be increased and flexibility of the composite structure is improved.

Highly flexible composite structures comprising a substrate and absorbent particles having a relatively low absorbent capacity are required in products which are intended to absorb relatively small amounts of fluids, such as pantiliners or sanitary napkins or light incontinence pads. A typical sanitary napkin has a basis weight of hydrogel-forming particles of about 54 g/m$^2$. Also, when the absorbent composite structure is used as the upper layer in a multilayer structure comprising multiple layers of hydrogel forming particles, such as described in European patent application no. 93305150.0 and 93309514.1, the relatively liquid permeable composite structure according to the invention, of relatively small absorbent capacity, ensures optimal liquid acquisition, distribution and storage.

By applying a low basis weight of hydrogel-forming particles to a flexible substrate, and firmly attaching these particles thereto by crosslink bonds, the flexibility of the composite structure is larger than for macrostructures comprising interparticle-cross linked aggregates that are attached to a flexible substrate. In use of an absorbent article that incorporates the absorbent composite structure according to the invention, increased flexibility will provide increased fit and increased comfort, due to good conformability to the anatomy of the user. The flexible substrate can be readily stored on a roll after formation, the roll being stored or being transported and being unwound in a production process for forming of an absorbent article.

The particles may be connected to both surfaces of the substrate such that the substrate is sandwiched between two layers of particles. Alternatively, a layer of particles may be sandwiched between two substrate layers and hence be protected against mechanical damage.

In one embodiment of an absorbent composite structure, the hydrogel-forming particles are non-uniformly dispersed on the substrate and are distributed onto the substrate in a pattern such as spots or stripes or other areas of varying basis weight. For instance, a substrate comprising an area of a low basis weight of hydrogel forming particles or comprising an area free of hydrogel forming particles, can advantageously be used as a liquid permeable upper layer in a multilayer structure such as disclosed in International patent application WO 92/11831 (Feist et al.) or WO 92/11830 (Noel et al.). In these multilayer structures the area of low basis weight can form a window through which liquid can enter to the lower layers. Alternatively, the composite structure having a central area of low basis weight of hydrogel-forming particles, can be used as a core for a catamenial product in which longitudinal liquid flow is promoted along the central area which acts as a liquid-directing channel such cores are disclosed in WO 94/02092 (Coles).

A further advantage of the absence of an inter-particle crosslinked aggregate, is that the composite structure can be mechanically deformed in a relatively fine line pattern for instance by ringrolling as described in U.S. Pat. No. 5,167,897 to impart a relatively large degree of extensibility to the composite structure, without the particles becoming detached from the substrate.

The absorbent composite structure according to the invention can advantageously be made elastically extensible. The substrate can freely expand and contract without being restrained by the hydrogel-forming particles, which remain firmly attached to the substrate upon stretching. In one embodiment such as described in U.S. application Ser. No. 08/096,092 (Osborn) the composite structure extends between 5% and 50% under forces of between 50 g and 1500 g. Elastically extensible absorbent structures which extend to 140% of their relaxed length under a force between 250 g and 800 g have been described in WO 93/01785 (Osborn et al.)

BRIEF DESCRIPTION OF THE DRAWINGS

The invention will be explained in detail with reference to the accompanying drawings. In the drawings.

DETAILED DESCRIPTION OF THE INVENTION

Figure 1:
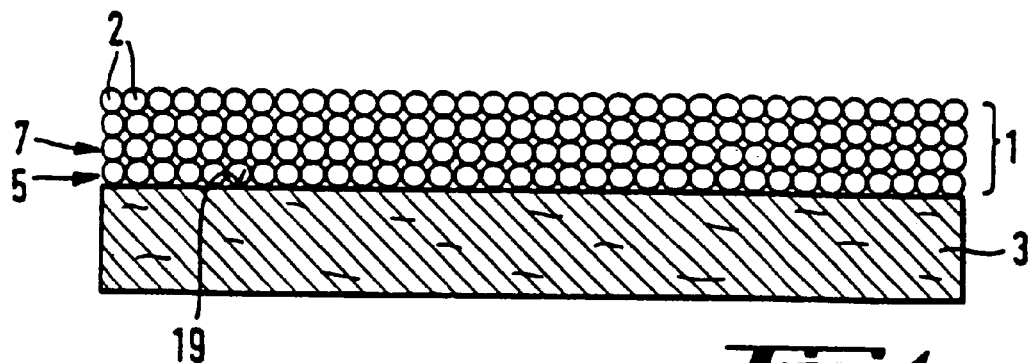
FIG. 1 shows a cross-sectional view of a known absorbent composite structure.

FIG. 1 shows a known composite absorbent structure such as described in U.S. application Ser. No. 08/142,258 (Hsueh). A macrostructure comprising an interparticle crosslinked absorbent aggregate 1 is bonded to a substrate 3. The crosslinked aggregate 1 is formed by interparticle crosslinked particles 2. The particles 2 are connected by crosslinking to form a macrostructure in the form of a self-supporting continuous layer. For stability and improved strength, this layer is connected to a substrate 3 by means of chemical bonding or by adhesive attachment. The crosslinked aggregate 1 is formed of hydrogel-forming particles which may have a diameter between 50 and 2000 microns. The thickness of the interparticle crosslinked aggregate is for instance between 250 microns and 10 millimeter. The crosslinked aggregate as shown in FIG. 1 extends across substantially the whole upper surface 19 of the substrate 3 and is self-supporting, i.e. it is not reduced into individual particles upon detaching the aggregate 1 from the substrate 3. The crosslinked aggregate 1 is formed by applying a first layer 5 of hydrogel-forming particles 2 on a conveyor or directly onto a substrate, such that these particles are in intimate mutual contact. The particles are transported underneath a sprayhead which applies a crosslinking agent to the particles to effect inter-particle is crosslinking. After cross-linking the first layer 5 of particles 2, the second layer 7 is deposited onto the first layer 2. This layer is attached by crosslinking with the particles of the first layer. Further crosslinking agent is applied to layer 7 in a second spraying station. In this way, several layers of particles 2 are connected to form the aggregate.

Figure 2:
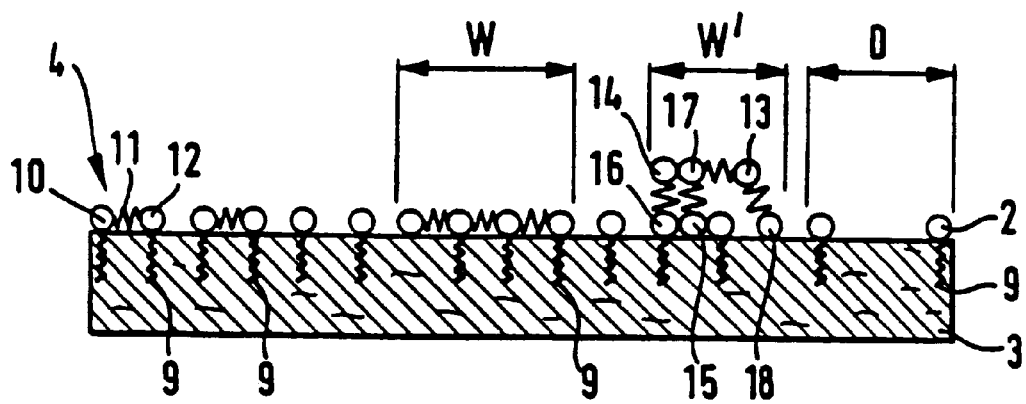
FIGS. 2–7 show cross-sectional views of embodiments of absorbent composite structures according to the invention.
Figure 3:
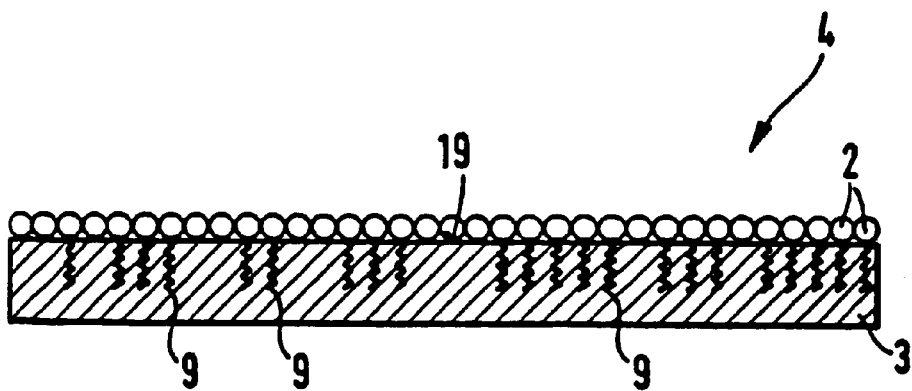

FIGS. 2 and 3 show an absorbent composite structure 4 according to the invention. The hydrogel-forming particles 2 are deposited onto the substrate 3 such that no coherent self-supporting crosslinked aggregate is formed. The particles 2 comprise crosslink bonds 9 with the cellulosic material of the substrate 3 and are attached via these bonds. For the particles 2 according to the invention, the crosslink bonds 9 between the molecules of the particles and the molecules of the substrate 3 form the attachment of the majority of particles, contrary to the structure according to FIG. 1, in which most particles are attached to the substrate 3 via other particles with which they form a crosslinked aggregate. In the absorbent composite structure 4 there is a degree of crosslinking between neighbouring particles, such as interparticle crosslink bond 11 between particles 10 and 12, wherein each particle 10 and 12 is located on the substrate 3. Other crosslink bonds may be formed between particles that are located on the substrate 3 and between particles that are located on top these particles. This is illustrated by particles 14 and 16, wherein particle 16 is connected to the substrate 3 via crosslink bond 9 and particle 14 is connected to particle 16 by a crosslink bond of the same type as crosslink bonds 9. Further crosslink bonds may be formed between particles 17 and 13 which are only indirectly connected to the substrate 3, and between particles 13 and 18, such that a small size aggregate is formed by interparticle crosslinked particles 13,14,15,16,17 and 18. It is important in all cases that the dimensions W, W' of the aggregates are such that no coherent, self-supporting agglomerated macrostructure is formed of circumscribed dry volume larger than 10 mm$^3$.

One way of making an absorbent composite structure as shown in FIG. 2, is by first aggregating the precursor particles 2 into aggregates of a largest circumscribed dry volume of 10 mm$^3$ and subsequently attaching these aggregates to the substrate while maintaining sufficient spacing between neighbouring aggregates to prevent crosslink bonds being formed between adjacent aggregates.

Alternatively, the hydrogel-forming particles 2 can be directly applied to the substrate 3 in a sufficiently low basis weight, such that the formation of inter-particle cross link bonds are limited. This can for example be achieved by applications of basis weights below 100 gm$^{-2}$ to the substrate 3.

Again, alternatively, the hydrogel-forming particles 2 may be applied to the substrate 3 in a substantially continuous layer, as shown in FIG. 3, the crosslinking agent for connecting the particles to the substrate 3 being applied in such a way that only the particle-substrate interface 19 is contacted by crosslinking agent. For instance, the cross linking agent can be applied to the upper surface of the substrate 3 prior to depositing particles 2 onto the substrate 3.

Absorbent Precursor Particles

The absorbent composite structures used in the present invention are formed from polymer materials capable of absorbing large quantities of liquids. (Such polymer materials are commonly referred to as "hydrogel", "hydrocolloid", or "superabsorbent" materials.) The hydrogel-forming particles preferably comprise substantially water-insoluble, absorbent hydrogel-forming, polymer material. The specific polymer materials will be discussed herein with respect to those forming the absorbent gelling particles (hereinafter also referred to as "precursor particles").

Although the precursor particles can have a size varying over a wide range, specific particle size distributions and sizes are preferred. For purposes of the present invention, particle size is defined for precursor particles that do not have a large greatest dimension/smallest dimension ratio such as fibers (e.g., granules, flakes, or pulverulents) as the dimension of a precursor particle which is determined by sieve size analysis. Thus, for example, a precursor particle that is retained on a standard #30 sieve with 600 micron openings is considered to have a particle size greater than 600 microns, a precursor particle that passes through the #30 sieve with 600 micron openings and is retained on a standard #35 sieve with 500 micron openings is considered to have a particle size between 500 and 600 microns, and a precursor particle that passes through a #35 sieve with 500 micron openings is considered to have a particle size less than 500 microns. In preferred embodiments of the present invention, the precursor particles will generally range in size from about 1 micron to about 2000 microns, more preferably from about 20 microns to about 1000 microns.

Further, for purposes of this invention, the mass average particle size of the precursor particles is important in determining the characteristics and properties of the resultant composite absorbent structures. The mass average particle size of a given sample of precursor particles is defined as the particle size which is the average particle size of the sample on a mass basis. A method for determining the mass average particle size of a sample is described in detail in U.S. application Ser. No. 08/142,258. The mass average particle size of the precursor particles will generally be from about 20 microns to about 1500 microns, more preferably from about 50 microns to about 1000 microns, most preferably from about 50 microns to about 800 microns. In especially preferred embodiments, the mass average particle sizes is from about 100 microns to about 250 microns. The particles can be substantially uniform in size and shape, or can be randomly or ordered in size and shape. In an exemplary embodiment, at least about 95% by weight of the precursor particles have a particle size between about 150 microns and about 300 microns. In an alternative embodiment, at least about 95% by weight of the precursor particles have a particle size between about 90 microns and about 180 microns. Narrow precursor particle size distributions are preferred because they result in a higher porosity absorbent composite structure due to the higher void fraction when densified versus broader precursor particle size distributions with equivalent mass average particle sizes.

The particle size of materials having a large greatest dimension/smallest dimension such as fibers is typically defined by their largest dimension. For example, if absorbent, polymeric fibers (i.e. hydrogel-forming fibers) are used in the composite absorbent structures, the length of the fibers is used to define the "particle size." (The denier and/or the diameter of the fibers can also be specified.) In exemplary embodiments of the present invention, the fibers have a length greater than about 5 mm, preferably between about 10 mm and about 100 mm, more preferably between about 10 mm and about 50 mm.

The precursor particles comprise substantially water-insoluble, absorbent hydrogel-forming, polymer material having a multiplicity of anionic, functional groups, such as sulfonic acid, and more typically carboxy, groups. Examples of polymer materials suitable for use as the precursor particles herein include those which are prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the precursor particles herein. Such non-acid monomers can include, for example, the water-soluble or water-dispersible esters of the acid-containing monomers, as well as monomers which contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrite groups and quaternary ammonium salt groups. These non-acid monomers are well-known materials and are described in greater detail, for example, in U.S. Pat. No. 4,076,663 (Masuda et al), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, a-chloroacrylic acid, a-cyanoacrylic acid, b-methylacrylic acid (crotonic acid), a-phenylacrylic acid, b-acryloxypropionic acid, sorbic acid, a-chlorosorbic acid, angelic acid, cinnamic acid, p-chloro cinnamic acid, b-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyltoluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxy propyl sulfonic acid and 2-acrylamide-2-methylpropane sulfonic acid.

Preferred polymer materials for use in the present invention contain carboxy groups. These polymers include hydrolyzed starch-acrylonitrile graft copolymers, partially neutralised starch-acrylonitrile graft copolymers, starch acrylic acid graft copolymers, partially neutralised starch-acrylic acid graft copolymers, saponified vinyl acetate-acrylic ester copolymers, hydrolysed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. Nos. 3,661,875, 4,076,663, 4,093,776, 4,666,983, and 4,734,478.

Most preferred polymer materials for use in making the precursor particles are slightly network crosslinked polymers of partially neutralised polyacrylic acids and starch derivatives thereof. Most preferably, the precursor particles comprise from about 50% to about 95%, preferably about 75%, neutralised, slightly network crosslinked, polyacrylic acid (i.e. poly (sodium acrylatelacrylic acid)). As described above, the precursor particles are preferably made from polymer materials that are slightly network crosslinked. Network crosslinking serves to render the polymer materials from which the precursor particles are made substantially water-insoluble and, in part, determines the absorptive capacity and extractable polymer content characteristics of the precursor particles and the resultant composite absorbent structures. Processes for network crosslinking the polymers and typical network crosslinking agents are described in greater detail in the hereinbefore-referenced U.S. Pat. No. 4,076,663.

The individual precursor particles can be formed in any conventional manner. Typical and preferred processes for producing the individual precursor particles are described in U.S. Pat. No. Re. 32,649 (Brandt et al), issued Apr. 19, 1988, U.S. Pat. No. 4,666,983 (Tsubakimoto et al), issued May 19, 1987, and U.S. Pat. No. 4,625,001 (Tsubakimoto et al), issued Nov. 25, 1986, all of which are incorporated by reference. Preferred methods for forming the precursor particles are those that involve aqueous solution or other solution polymerization methods. As described in the above-referenced U.S. Pat. No. Re. 32,649, aqueous solution polymerization involves the use of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. The mass of polymer material thereby formed is then pulverized or chopped to form the individual precursor particles.

More specifically, the aqueous solution polymerization method for producing the individual precursor particles comprises the preparation of an aqueous reaction mixture in which to carry out polymerization to form the desired precursor particles. One element of such a reaction mixture is the acid group-containing monomer material which will form the "backbone" of the precursor particles to be produced. The reaction mixture will generally comprise about 100 parts by weight of the monomer material. Another component of the aqueous reaction mixture comprises a network crosslinking agent. Network crosslinking agents useful in forming the precursor particles are described in more detail in the above-referenced U.S. Pat. No. Re. 32,649, U.S. Pat. Nos. 4,666,983, and 4,625,001. The network crosslinking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer material). An optional component of the aqueous reaction mixture comprises a free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomer materials including esters of the essential unsaturated acidic functional group-containing monomers or other co-monomers containing no carboxylic or sulfonic acid functionalities at all.

The aqueous reaction mixture is subjected to polymerization conditions which are sufficient to produce in the mixture substantially water-insoluble, absorbent, hydrogel-forming, slightly network crosslinked polymer materials. The polymerization conditions are also discussed in more detail in the three above-referenced patents. Such polymerization conditions generally involve heating (thermal activation techniques) to a polymerization temperature from about 0° C. to about 100° C. , more preferably from about 5° C. to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques.

The acid functional groups of the polymer materials formed in the aqueous reaction mixture are also preferably neutralized. Neutralization can be carried out in any conventional manner which results in at least about 25 mole percent, and more preferably at least about 50 mole percent, of the total monomer utilized to form the polymer material being acid group-containing monomers that are neutralized with a salt-forming cation. Such salt-forming cations include, for example, alkali metals, ammonium, substituted ammonium and amines as discussed in further detail in the above-references U.S. Pat. No. Re. 32,649. While it is preferred that the precursor particles be manufactured using an aqueous solution polymerization process, it is also possible to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. The resultant precursor particles are generally spherical in shape. Inverse suspension polymerization procedures are described in greater detail in U.S. Pat. No. 4,340,706 (Obaysashi et al), issued Jul. 20, 1982, U.S. Pat. No. 4,506,052 (Flesher et al), issued Mar. 19, 1985, and U.S. Pat. No. 4,735,987 (Morita et al), issued Apr. 5, 1988, all of which are incorporated by reference.

The precursor particles are preferably substantially dry. The term "substantially dry" is used herein to mean that the precursor particles have a liquid content, typically water or other solution content, less than about 50%, preferably less than about 20%, more preferably less than about 10%, by weight of the precursor particles. Most preferably, the liquid content of the precursor particles is in the range of from about 0.01% to about 5% by weight of the precursor particles. The individual precursor particles can be dried by any conventional method such as by heating. Alternatively, when the precursor particles are formed using an aqueous reaction mixture, water can be removed from the reaction mixture by azeotropic distillation. The polymer-containing aqueous reaction mixture can also be treated with a dewatering solvent such as methanol. Combinations of these drying procedures can also be used. The dewatered mass of polymer material can then be chopped or pulverized to form substantially dry precursor particles of substantially water-insoluble, absorbent, hydrogel-forming, polymer material.

Preferred precursor particles of the present invention are those which exhibit a high absorptive capacity so that the resultant macrostructure formed from such precursor particles also has a high absorptive capacity. Absorptive capacity refers to the capacity of a given polymer material to absorb liquids with which it comes into contact. Absorptive capacity can vary significantly with the nature of the liquid being absorbed and with the manner in which the liquid contacts the polymer material. For purposes of this invention, Absorptive Capacity is defined in terms of the amount of Synthetic Urine absorbed by any given polymer material in terms of grams of Synthetic Urine per gram of polymer material in a procedure such as defined in the Test Methods section of U.S. application Ser. No. 08/142,258 (Hsueh). Preferred precursor particles of the present invention are those which have an Absorptive Capacity of at least about 20 grams, more preferably at least about 25 grams, of Synthetic Urine per gram of polymer material. Typically, the polymer materials of the precursor particles herein have an Absorptive Capacity of from about 20 grams to about 70 grams of Synthetic Urine per gram of polymer material. Precursor particles having this relatively high absorptive capacity characteristic produce macrostructures that are especially useful in absorbent products, absorbent members, and absorbent articles since the resultant macrostructures formed from such precursor particles can, by definition, hold desirably high amounts of discharged body exudates such as urine.

While all of the precursor particles may be typically formed from the same polymer material with the same properties, this need not be the case. For example, some precursor particles can comprise a starch-acrylic acid graft copolymer while other precursor particles can comprise a slightly network crosslinked polymer of partially neutralized polyacrylic acid. Further, the precursor particles can vary in size, shape, absorptive capacity, or any other property or characteristic. In a preferred embodiment of the present invention, the precursor particles consist essentially of slightly network crosslinked polymers of partially neutralized polyacrylic acid.

In another embodiment of the present invention, the precursor particles can themselves be crosslinked at least at a portion of, preferably substantially all of, their surfaces, prior to forming the precursor particles into an absorbent composite structure. The surface crosslinking of precursor particles can be made by any of the crosslinking agents described hereinafter. Preferred crosslinking agents preferably have relatively large molecular size, and are preferably cationic. Such a crosslinking agent is unable to penetrate inside the absorbent particles, and therefore can only react with polymer material at the surface thereof effectively. Most preferably, the crosslinking agent is a cationic amino-epichlorohydrin adduct. Surface crosslinked hydrogel-forming absorbent polymers have a higher level of crosslinking in the vicinity of the surface than in the interior. As used herein, "surface" describes the outer-facing boundaries of the particle, fiber, etc. For porous hydrogel-forming absorbent polymers (e.g., porous particles, etc.), exposed internal boundaries can also be included. By a higher level of crosslinking at the surface, it is meant that the level of functional crosslinks for the hydrogel-forming absorbent polymer in the vicinity of the surface is generally higher than the level of functional crosslinks for the polymer in the interior.

The gradation in crosslinking from surface to interior can vary, both in depth and profile. Thus, for example, the depth of surface crosslinking can be shallow, with a relatively sharp transition to a lower level of crosslinking. Alternatively, for example, the depth of surface crosslinking can be a significant fraction of the dimensions of the hydrogel-forming absorbent polymer, with a broader transition.

Depending on size, shape, porosity as well as functional considerations, the degree and gradient of surface crosslinking can vary within a given hydrogel-forming absorbent polymer. For particulate hydrogel-forming absorbent polymers, surface crosslinking can vary with particle size, porosity, etc. Depending on variations in surface:volume ratio within the hydrogel-forming absorbent polymer (e.g., between small and large particles), it is not unusual for the overall level of crosslinking to vary within the material (e.g., be greater for smaller particles).

Surface crosslinking is generally accomplished after the final boundaries of the hydrogel-forming absorbent polymer are essentially established (e.g., by grinding, extruding, foaming, etc.) However, it is also possible to effect surface crosslinking concurrent with the creation of final boundaries. Furthermore, some additional changes in boundaries can occur even after surface crosslinks are introduced.

A number of processes for introducing surface crosslinks are disclosed in the art. These include those where: (i) a di- or poly-functional reagent(s) (e.g., glycerol, 1,3-dioxolan-2-one, polyvalent metal ions, polyquaternary amines) capable of reacting with existing functional groups within the hydrogel-forming absorbent polymer is applied to the surface of the hydrogel-forming absorbent polymer; (ii) a dior poly-functional reagent that is capable of reacting with other added reagents and possibly existing functional groups within the hydrogel-forming absorbent polymer such as to increase the level of crosslinking at the surface is applied to the surface (e.g., the addition of monomer plus crosslinker and the initiation of a second polymerization reaction); (iii) no additional polyfunctional reagents are added, but additional reaction(s) is induced amongst existing components within the hydrogel-forming absorbent polymer either during or after the primary polymerization process such as to generate a higher level of crosslinking at or near the surface (e.g., heating to induce the formation of anhydride and or esters crosslinks between existing polymer carboxylic acid and/or hydroxyl groups and suspension polymerization processes wherein the crosslinker is inherently present at higher levels near the surface); and (iv) other materials are added to the surface such as to induce a higher level of crosslinking or otherwise reduce the surface deformability of the resultant hydrogel. Combinations of these surface crosslinking processes either concurrently or in sequence can also be employed. In addition to crosslinking reagents, other components can be added to the surface to aid/control the distribution of crosslinking (e.g., the spreading and penetration of the surface crosslinking reagents.)

Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992; all of which are incorporated by reference.

Crosslinking Agent

A crosslinking agent is used to crosslink the polymer material of the precursor particles 2 to the absorbent substrate 3. A suitable crosslinking agent can be a nonionic crosslinking agents described in U.S. Pat. No. 5,102,597 (Roe et al), issued Apr. 7, 1992. These nonionic crosslinking agents include polyhydric alcohols (e.g., glycerol), polyaziridine compounds (e.g., 2,2-bishydroxymethyl butanoltris[3-(1-aziridine) propionate]), haloepoxy compounds (e.g., epicholorhydrin), polyaldehyde compounds (e.g., glutaraldehyde), polyamine compounds (e.g., ethylene amine), and polyisocyanate compounds (e.g., 2,4-toluene diisocyanate), preferably glycerol.

Preferred crosslinking agents are those which primarily provide crosslinking at portions of the surface of the absorbent precursor particles. Such crosslinking agents preferably have relatively large molecular size, and are preferably cationic. As a result, it is believed, such a crosslinking agent is unable to penetrate inside the absorbent particles, and therefore can only react with polymer material at the surface thereof effectively. It is possible that some such larger crosslinking agent can penetrate into the particle when the particle is swelled via the swelling agent.

Another preferred crosslinking agent is one which reacts very rapidly with the anionic, typically carboxy functional groups of the polymer material of the absorbent particles, even at a room temperature range (e.g., at from about 13° C. to about 33° C.). As a result, fairly modest levels (e.g., as low as about 1% by weight of the particles) of such crosslinking agent are required to provide effective surface crosslinking of the polymer material present in the absorbent precursor particles.

A preferred crosslinking agent of the present invention, however, is an adduct of epichlorohydrin with certain types of monomeric or polymeric amines. These amino-epichlorohydrin adducts react with the polymer material of the absorbent precursor particles, and in particular the anionic, typically carboxy, functional groups of these polymer materials to form a covalent, ester-type bond. In other words, the amino-epichlorohydrin adduct serves to crosslink the polymer material present in the absorbent precursor particles. (The portions of the absorbent particle containing polymer material that has been effectively crosslinked with the amino-epichlorohydrin adduct swell less in the presence of aqueous body fluids relative to the other uncrosslinked portions of the particle.) Such cationic amino-epichlorohydrin adduct, especially a polymeric resin version, is relatively large such that preferential surface crosslinking is achieved. Such adduct with its cationic functional groups (e.g., azetedinium groups) can react rapidly with the polymer material at the room temperature range of preferably from about 13° C. to about 33° C., more preferably from about 18° C. to about 28° C., most preferably about 23° C.

As used herein, "cationic amino-epichlorohydrin adduct" refers to the reaction product between epichlorohydrin and a monomeric or polymeric amine such that the resulting reaction product has at least two cationic functional groups. These adducts can be in the form of monomeric compounds (e.g., the reaction product of epichlorohydrin and ethylene diamine), or can be in polymeric form (e.g., the reaction product between epichlorohydrin, and polyamide-polyamines or polyethyleneimines). The polymeric versions of these cationic amino-epichlorohydrin adducts are typically referred to as "resins."

One type of amino compound which can be reacted with epichlorohydrin to form adducts useful in the present invention comprises monomeric di-, tri- and higher amines having primary or secondary amino groups in their structures. Examples of useful diamines of this type include bis-2-aminoethyl ether, N,N-dimethylethylenediamine, piperazine, and ethylenediamine. Examples of useful triamines of this type include N-aminoethyl piperazine, and dialkylene triamines such as diethylenetriamine, and dipropylenetriamine.

Such amine materials are reacted with epichlorohydrin to form the cationic amino-epichlorohydrin adducts useful as crosslinking agents herein. Preparation of these adducts, as well as a more complete description of the adducts themselves, can be found in U.S. Pat. No. 4,310,593 (Gross), issued Jan. 12, 1982, and in Ross et al, J. Organic Chemistry, Vol. 29, pp. 824–826 (1964). Both of these documents are incorporated by reference.

In addition to monomeric amines, polymeric amines such as polyethyleneimines can also be used as the amino compound. A particularly desirable amino compound which can be reacted with epichlorohydrin to form preferred cationic polymeric adduct resins useful herein comprise certain polyamide-polyamines derived from polyalkylene polyamines and saturated C3–C10 dibasic carboxylic acids. Epichlorohydrin/polyamide-polyamine adducts of this kind are water-soluble, thermosetting cationic polymers which are well known in the art as wet strength resins for paper products.

In the preparation of polyamide-polyamines used to form this preferred class of cationic polymeric resins, a dicarboxylic acid is first reacted with a polyalkylene-polyamine, preferably in aqueous solution, under conditions such as to produce a water-soluble, long chain polyamide containing the recurring groups —NH(CnH2nHN)x—CORCO— where n and x are each 2 or more and R is the C1 to C8 alkylene group of the dicarboxylic acid.

A variety of polyalkylene polyamines including polyethylene polyamines, polypropylene polyamines, polybutylene polyamines and so on can be employed to prepare the polyamide-polyamine, of which the polyethylene polyamines represent an economically preferred class. More specifically, preferred polyalkylene polyamines used to prepare the cationic polymeric resins herein are polyamines containing two primary amine groups and at least one secondary amine group in which the nitrogen atoms are linked together by groups of the formula —CnH2n— where n is a small integer greater than unity and the number of such groups in the molecule ranges from two up to about eight and preferably up to about four. The nitrogen atoms can be attached to adjacent carbon atoms in the group —CnH2n— or to carbon atoms further apart, but not to the same carbon atom. Also contemplated is the use of such polyamines as diethylenetriamine, triethylene tetramine, tetraethylenepentamine, dipropylenetriamine, and the like, which can be obtained in reasonably pure form. Of all the foregoing, the most preferred are the polyethylene polyamines containing from two to four ethylene groups, two primary amine groups, and from one to three secondary amine groups.

Also contemplated for use herein are polyamine precursor materials containing at least three amino groups with at least one of these groups being a tertiary amino group. Suitable polyamines of this type include methyl bis(3-aminopropyl) amine, methyl bis(2-aminoethyl)amine, N-(2-aminoethyl) piperazine, 4,7-dimethyltriethylenetetramine and the like.

The dicarboxylic acids which can be reacted with the foregoing polyamines to form the polyamide-polyamine precursors of the preferred cationic polymeric resins useful herein comprise the saturated aliphatic C3–C10 dicarboxylic acids. More preferred are those containing from 3 to 8 carbon atoms, such as malonic, succinic, glutaric, adipic, and so on, together with diglycolic acid. Of these, diglycolic acid and the saturated aliphatic dicarboxylic acids having from 4 to 6 carbon atoms in the molecule, namely, succinic, glutaric and adipic are most preferred. Blends of two or more of these dicarboxylic acids can also be used, as well as blends of one or more of these with higher saturated aliphatic dicarboxylic acids such as azelaic and sebacic, as long as the resulting long chain polyamide-polyamine is water-soluble or at least water-dispersible.

The polyamide-polyamine materials prepared from the foregoing polyamines and dicarboxylic acids are reacted with epichlorohydrin to form the cationic polymeric aminoepichlorohydrin resins preferred for use herein as the crosslinking agent. Preparation of such materials is describe in greater detail in U.S. Pat. No. 2,926,116 (Keim), issued Feb. 23, 1960, U.S. Pat. No. 2,926,154 (Keim), issued Feb. 23, 1960, and U.S. Pat. No. 3,332,901 (Keim), issued Jul. 25, 1967, all of which are incorporated by reference.

The cationic polyamide-polyamine-epichlorohydrin resins preferred for use herein as crosslinking agents are commercially marketed by Hercules Inc. under the trade name Kymene®. Especially useful are Kymene® 557H, Kymene® 557LX and Kymene® 557 Plus, which are the epichlorohydrin adducts of polyamidepolyamines which are the reaction products of diethylenetriamine and adipic acid. They are typically marketed in the form of aqueous solutions of the cationic resin material containing from about 10% to about 33% by weight of the resin active.

Substrate Layer

The substrate layer provides a variety of functions. Primarily, it serves as a supporting means for the precursor particles 2. It can also serve as a distributing means for improving the distribution of applied liquids to be absorbed into the absorbent composite structure. Preferably, the liquid distribution properties of the substrate layer 3 are substantially greater than those of the precursor particles 2, such that the absorbent composite structure has improved liquid distribution properties relative to the layer of precursor particles 2 alone. In preferred embodiments, the substrate layer 3 comprises a plurality of capillary elements having a length, preferably arranged substantially in parallel, for improving the distribution of the liquid along the lengths thereof.

The substrate is preferably one which has excellent wet strength, and can impart improved wet strength and wet integrity to the absorbent composite structure; that is, the substrate is effective as a supporting means after the precursor particles 2 and the substrate itself have become wet with liquid. Support for the bonded gelling particles is needed especially in this situation, where the gelling particles begin to swell after absorbing liquid. Such support is especially important when the absorbent composite is used in an absorbent article such as a diaper or catamenial product where external forces can also act upon the structure to cause precursor particles that are not firmly attached to the substrate to become detached.

The substrate layer can be selected from various materials known in the art such as cellulose fibers, nonwoven webs, tissue webs, foams, polyacrylate fibers, apertured polymeric webs, synthetic fibers, metallic foils, elastomers, and the like. Most such substrates can serve both as a distributing means and a supporting means for the absorbent macrostructure layer. Preferably, the substrate layer is comprised of cellulosic material or a material having cellulosic functionality. Preferred substrates for use as a fluid distributing means can be selected from cellulosic materials, fibrous webs, cellulosic fibrous webs, solid foams, cellulosic foams, and polyvinyl alcohol foams. Preferred substrates for use as a supporting means can be selected from cellulosic materials, fibrous webs, nonwoven webs, fabrics, cellulosic fibrous webs, solid foams, cellulosic foams, and polyvinyl alcohol foams.

The substrate layer is preferably flexible and pliable to encourage such properties in the resulting absorbent composite. A substrate layer can be substantially resilient and non-stretchable, or it can be stretchable or deformable to a varying extent in response to forces exerted normal to and in the plane of the surface of the substrate.

The thickness and basis weight (weight per unit area of substrate) of a substrate material will vary depending on the type of substrate and the desired properties. A substrate can also comprises a plurality of individual sheets, or plies, of a particular substrate material, or a combination of one or more substrate layers in a laminate. As a typical substrate, a Bounty® sheet has a thickness of from about 0.02 mm to about 1.2 mm, more preferably from about 0.3 mm to about 0.8 mm, and a basis weight of from about 5 gm/m² to about 100 gm/m², more preferably from about 10 gm/m² to about 60 gm/m², and most preferably from about 15 gm/m² to about 40 gm/m². As another typical substrate, a cellulose foam has a dry compressed thickness of from about 0.5 mm to about 3.0 mm, more preferably from about 0.8 mm to about 2.0 mm, a wet expanded thickness of from about 0.8 mm to about 6.0 mm, more preferably from about 1.0 mm to about 5.0 mm, and a basis weight of from about 50 gm/m² to about 2,000 gm/m², more preferably from about 100 gm/m² to about 1,000 gm/m².

Substrates for use as support means typically have a dry tensile strength of from about 500 gm/in to about 8,000 gm/in, though more preferably from about 1,000 gm/in to about 3,000 gm/in, a wet tensile strength of from about 200 gm/in to about 5,000 gm/in, though more preferably from about 400 gm/in to about 1,000 gm/in, and a wet burst strength of from about 100 gm to about 2,000 gm, though more preferably from about 200 gm to about 1,000 gm.

In preferred embodiments, the substrate layer comprises a cellulosic fibrous web such as paper towelling and paper tissue. Examples of such cellulosic fibrous webs are disclosed in U.S. Pat. No. 3,953,638, issued Apr. 27, 1976, U.S. Pat. No. 4,469,735, issued Sep. 4, 1984, U.S. Pat. No. 4,468,428, issued Aug. 28, 1984, and U.S. Pat. No. 4,986,882, issued Jan. 22, 1991, all herein incorporated by reference. A preferred example of such is Bounty® paper towel, commercially marketed in the U.S. by The Procter & Gamble Company. Another preferred example of such is Kinocloth® paper tissue, commercially marketed in the U.S. and Japan by Honshu Paper Go., Ltd.. Bounty® and Kinocloth® are hydrophilic and have good distribution and wicking properties, as well as good wet integrity.

In another preferred embodiment, the substrate layer comprises a cellulosic foam. In general, a cellulosic foam will provide a higher liquid wicking rate over a longer wicking distance than a cellulosic fibrous web. Preferably, the cellulosic foam is in a compressed state so as to further improve its wicking and fluid distribution properties. Suitable cellulose foam can be made of regenerated rayon fibers by well-known methods, such as those disclosed in European patent application EP-A-293,208. Such cellulose foams have numerous small cells, the size of which affect the capillarity and absorptivity of the foam. The cellulose foam layer will ordinarily, and preferably, expand when wet. A preferred cellulosic foam is one which has been compressed in the dry state prior to use. The average pore size of the cellulose foam layer can be determin ed by the compression. In preferred embodiments, the average pore size of the cellulose foam layer, as measured in the dry state after any compression, is from about 1 micron to about 1000 microns, preferably from about 1 micron to about 200 microns, more preferably from about 5 microns to about 70 microns. A preferred compressed cellulose foam layer has a density of from about 0.1 g/cc (about 0.05 g/in³) to about 0.8 g/cc (about 0.41 g/in³) and has a compressed thickness (in sheet form) of from about 2 mm to about 5 mm. In general, better wicking properties can be obtained by using a foam layer having a higher density, or a smaller pore size. When such compressed cellulose foam layer contacts with liquids, the pore size of the foam begins to expand whereby the thickness of the foam layer become increased.

Absorbent foam substrates, particularly compressed cellulose foam substrates, are highly preferred substrates in the absorbent composites of the present invention. In addition to having excellent dry and wet strength and integrity, cellulose foam substrates, specifically in the form of sheets, have excellent capillarity and fluid wicking properties. When liquid such as water or body exudate is deposited onto the surface of an absorbent composite comprising a foam cellulose substrate the liquid passing through the layer of hydrogel-forming particles and into the cellulose foam substrate is distributed quickly outward toward dry foam areas in cellulose foam layer due to its capillary suction. That is, as the cellulose foam absorbs water or aqueous liquids, the cellulose foam cell structure begins to expand. Since the dry foam areas have a cell structures which are still compressed and which are smaller than the cells of the wetted areas, fluids readily wick into the dry foam areas. Such cellulose foam substrates are characterized by excellent fluid wicking and distribution. Specifically, such cellulose foam substrates have fast wicking ratio or speed (for example, up to at least 12 cm wicking distance in 4 minutes in a vertical wicking test) and long wicking distance capability (for example, from about 20 cm to about 30 cm in the first one hour in a vertical wicking test).

In yet another embodiment, the substrate layer can be a cellulose foam substrate formed by depositing cellulose foam particles (or granules). The cellulose foam particles have an average volume of at least about 0.1 mm³, preferably from about 1.0 mm³ to about 125 mm³. Preferably, the cellulose foam particles are deposited and compacted on an absorbent macrostructure layer.

A cellulose foam substrate is particular preferred when using the absorbent composite of the present invention in an absorbent catamenial article. When blood is deposited onto a cellulose foam substrate layer of an absorbent composite, the cellulose foam substrate can serve to acquire the blood, filter aggregates from the blood, and distribute the remaining liquid portion of the blood to the absorbent macrostructure layer below. The cellulose foam substrate may be provided with a plurality of slits in increase its flexibility.

In yet another preferred embodiment, the substrate layer comprises a compressed or non-compressed polyvinyl alcohol foam. In general, such foam preferably has properties and structure substantially as the cellulosic foam above.

Bonding Between the Hydrogel-Forming Particles and Substrate Layer

The bonding or interconnection between the hydrogel-forming particles 2 and the substrate layer 3 is effected by a crosslinking agent capable of crosslinking the absorbent molecules of the absorbent gelling particles 2. Any crosslinking agent which is known in the art and is capable of crosslinking the absorbent molecules of the hydrogel-forming particles can be used as a bonding agent. A suitable crosslinking agent can be a nonionic crosslinking agents described in U.S. Pat. No. 5,102,597 (Roe et al), issued Apr. 7, 1992. These nonionic crosslinking agents include polyhydric alcohols (e.g., glycerol), polyaziridine compounds (e.g., 2,2-bishydroxymethyl butanoltris[3-(1-aziridine) propionate]), haloepoxy compounds (e.g., epicholorhydrin), polyaldehyde compounds (e.g., glutaraldehyde), polyamine compounds (e.g., ethylene amine), and polyisocyanate compounds (e.g., 2,4-toluene diisocyanate), preferably glycerol.

In a preferred embodiment where the substrate layer 3 comprises cellulosic material or has cellulosic activity at least at the surface thereof, an amino-epichlorohydrin adduct is preferably used as a chemical bonding means between the cellulosic substrate and the surfaces of the hydrogel-forming particles. The amino-epichlorohydrin adduct can chemically bond to carboxyl and hydroxyl groups in the cellulosic material and to the polymer material of the absorbent precursor particles, as well as to other amino-epichlorohydrin adduct molecules. Such chemical bonding can be hydrogen bonding, ionic/coulombic bonding, polymer entanglement bonding, and covalent bonding. In this manner, the amino-epichlorohydrin adduct can chemically bond together the substrate to the particles 2. The amino-epichlorohydrin adduct preferred for use herein as a bonding agent is Kymene®. Especially useful are Kymene® 557H, Kymene® 557LX and Kymene® 557 Plus. These are the epichlorohydrin adducts of polyamidepolyamine, which is the reaction product of diethylenetriamine and adipic acid.

Figure 4:
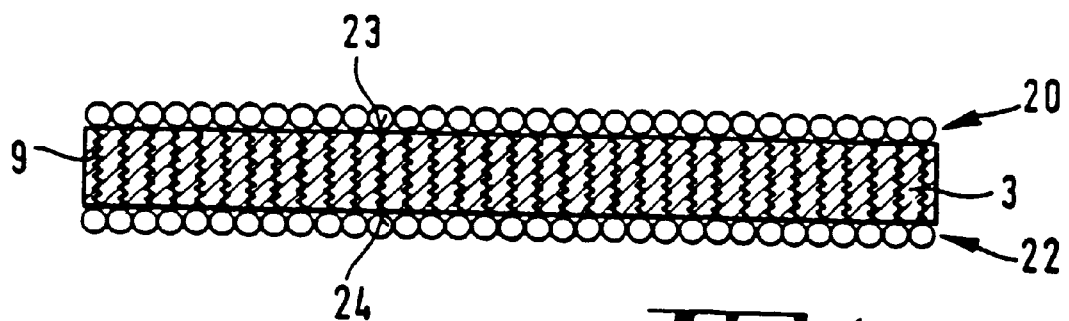

FIG. 4 shows a composite absorbent structure comprising two layers 20, 22 of hydrogel-forming particles. The particles are applied to the upper surface 23 and lower surface 24 of the substrate layer 3. The particles 2 in the layers 20 and 22 may be identical, but can also differ in physical and/or chemical properties.

For instance, the particles in the upper layer 20 may be of relatively large particle size such as between 400 and 800 microns, the particles in the lower layer 22 being chemically identical to the particles in layer 20 but being of smaller particle size, for instance below 250 microns.

The particles 2 in the lower layer 22 may be applied in larger basis weight than the particles in the lower layer. For instance the upper layer 20 may comprise a basis weight up to 100 g/m$^2$, the lower layer 24 comprising a basis weight between 200 and 400 g/m$^2$. Useful multilayer structures in which the composite structure can be used as the top layer have been described in European application no. 94111955.4 (Bogdanski).

Also, the degree in interparticle crosslinking between the particles in the lower layer may be different from the degree in interparticle crosslinking between the particles in the upper layer. This may be effected by applying a lower basis weight of hydrogel-forming particles to the upper surface 23 of the substrate 3, or by application of a different concentration of inter-particle crosslinking agent to the lower layer 22 of hydrogel-forming particles.

The crosslinking agent that bonds the particles 2 to the substrate 3, can also effect surface crosslinking of the particles 2. Increased surface crosslinking of the particles 2 will lead to improved absorption of liquids under pressure (between 0.3 and 1.0 psi) but to reduced Teabag Centrifuge Capacity. A test for measuring the absorption under pressure and Teabag Centrifuge Capacity has been described in European application no. 93309614.1. Generally, it is preferred that the hydrogel-forming particles in the upper layer 20 have a high liquid absorption against pressure, and do not easily deform so that an open structure is maintained. This can be achieved by increasing the degree of surface-crosslinking of the hydrogel-forming particles in the upper layer by controlling the amount of crosslinking agent used to bond the particles 2 to the substrate 3.

Alternatively, the chemical properties of the hydrogel-forming materials may be different, such that the upper layer comprises absorbent gelling materials of relatively slow speed and the lower layer comprises fast absorbing particles.

Preferably, the hydrogel-forming particles of the upper layer of an absorbent core should be relatively permeable and maintain an open structure, whereas the hydrogel-forming particles in the lower layers of an absorbent core may be less permeable.

Figure 5:
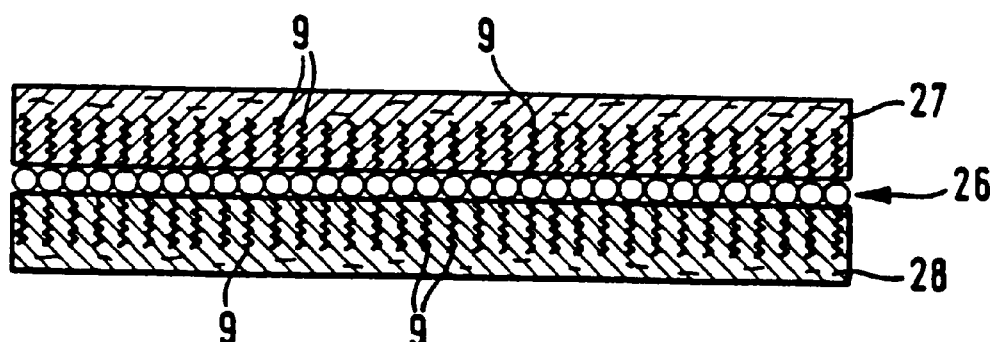

FIG. 5 shows an embodiment in which a layer 26 of hydrogel-forming particles is sandwiched between two substrate layers 27,28. The crosslink bonds 9 connecting the particles 2 of each layer 27,28 to the substrate layers 27,28 hold the combined layers 26,27 28 together such that an integrated structure is formed. An advantage of such a structure is that a pre-formed absorption body is formed which can, due to its flexibility, be stored on a roll, the layer 26 being protected by both layers 27,28 from becoming detached by chaffing, abrasion or mechanical impact.

Figure 6:
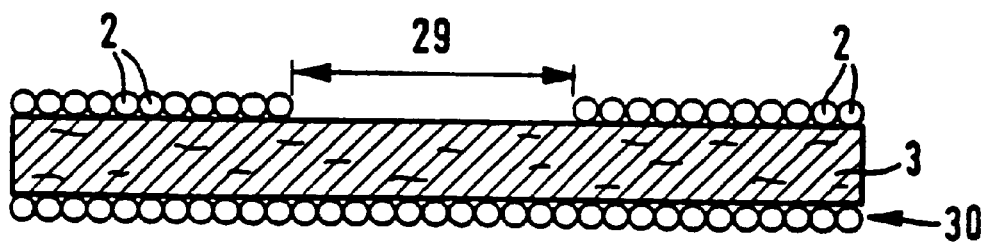

FIG. 6 shows an embodiment in which the substrate in specific areas 29 is not covered with hydrogel-forming particles 2, such that a window is formed through which liquids can enter into the substrate 3 and be transported within the substrate 3 across the lower layer 30.

Figure 7:
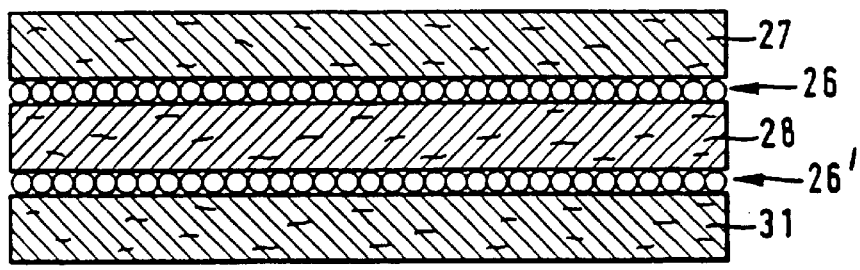

FIG. 7 shows an integrated multilayer structure comprising two layers of hydrogel-forming particles 26,26' sandwiched between three substrate layers 27,28,31.

Multilayer Core Comprising a Composite Absorbent Structure as an Upper Layer

Figure 8:
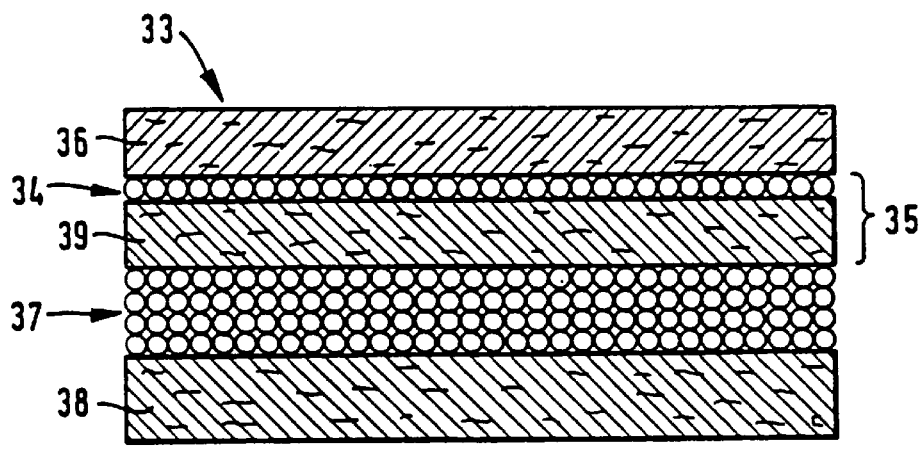
FIG. 8 shows a cross-sectional view of an absorbent core comprising an absorbent composite structure according to the invention.

FIG. 8 shows an embodiment of an absorbent core 33 comprising a multilayer structure in which the absorbent composite structure 35 is comprised and forms the second and third layer from the top of the core 33.

It is thought that the combination of materials and layers as shown in FIG. 8, provides a useful optimisation of the functionalities of the materials. In particular, it is thought to allow saturation of the hydrogel-forming material first in the region 37 of the core 33 furthest away from the wearer's body, and then gradually closer to the wearer's body until the core has reached its maximum capacity. This is achieved by providing an upper assembly or structure 34,36 which acts initially as an acquisition/distribution structure and that is relatively permeable to body discharges. The discharges therefore pass relatively quickly through the first layer 34 of superabsorbent, and into the lower assembly 37,39 which acts as a storage reservoir and also effects further distribution in layer 39. By preferentially arranging the second hydrogel-forming material 37 in the lower part 37 of the lower assembly 37,39, so that the upper part 39 has a low, preferably a zero concentration of hydrogel-forming material, void space is provided in the lower assembly that can promote the storage capacity of that assembly. By using second hydrogel-forming material 37 having an Absorption Against Pressure value of at least 15 g/g at 50 g/cm$^2$ pressure, good storage retention is achieved.

Liquid that is not adequately absorbed into the second hydrogel-forming material 37 can subsequently be absorbed in the first hydrogel-forming material 34. The provision of this material as a layer beneath the acquisition layer 36 has the advantage that this first hydrogel-forming material 34 acts to dry out the acquisition layer 36 as to minimise rewet and to improve skin dryness.

In order to achieve the desired performance characteristics it is necessary to select appropriate combinations of various materials in the core, as well as their amounts. The following description refers to suitable materials and by subjecting appropriate test articles made from them to the specified tests, and modifying the articles when necessary to achieve the required test results, cores according to the invention can be achieved.

For instance to achieve the above described fluid handling advantages the first assembly 34,36 should be sufficiently open, or permeable, relative to the second structure 37,39 to allow quick passage of body discharges through the first structure and into the second structure. However, the first structure 34, 36 should not be too open as this could lead to a higher risk of gel-blocking of the hydrogel-forming material 37 in the second structure, thereby under-utilising the absorbent capacity in that structure. A balance should be struck.

Upper Assembly

This comprises the acquisition layer 36 and a layer 34 of first hydrogel-forming particles.

The acquisition layer 36 is the upper effective layer of the absorbent core or other body excluding any tissue or topsheet if present). It is generally substantially free of hydrogel-forming material. If hydrogel-forming material is included, the amount should be kept low (for instance as in WO91/11163) but preferably the layer is wholly free of hydrogel-forming material, at least in the upper half, and generally throughout most or all of its thickness. The layer may be of foam or other suitable porous or capillary material but is usually formed of first fibrous material.

Suitable materials and properties of this upper layer, and methods of making it, are described in WO91/11163.

This upper layer 35 preferably has a Wet Compressibility of at least about 5 cm$^3$/g and a Drip Capacity of at least 10 g/g. Fibrous material of the defined Wet Compressibility and the defined drip capacity maintains its openness, or void volume, when wetted by, for example, urine. The provision of such a permanently open fibrous layer having a high drip capacity in the core means that not only does the core acquire body discharges, such as urine, rapidly, but the layer also has the potential to transfer these discharges into the subjacent structure of first particulate hydrogel-forming material relatively quickly.

The first fibrous material can be any fibrous material that has a suitable resistance to load when wet, i.e. is able to maintain satisfactory void volume under such conditions and this is defined herein as Wet Compressibility which is measured by the Wet Compressibility test described in detail in European patent application no. 93309614.1.

The "Wet Compressibility", or void volume per gram of wetted fibrous material under a 77.5 g cm$^{-2}$ (1.1 psi) load, of the first fibrous material is preferably at least 5 cm$^3$ g$^{-1}$, preferably at least 6 cm$^3$ g$^{-1}$, and most preferably at least 6.5 cm$^3$ g$^{-1}$, e.g., up to 8 or even 10 cm$^3$ g$^{-1}$ or more.

The first fibrous material preferably has a "Drip Capacity" of at least 10 ml g$^{-1}$, preferably at least 15 ml g$^{-1}$, and most preferably at least 20 ml g$^{-1}$, e.g., up to 25 or even 30 ml g$^{-1}$. The "Drip Capacity" is a measure of the ability of a fibre matrix to receive synthetic urine at a loading point, transfer it away from that point and then hold it within the matrix. The "Drip Capacity" is measured by the Drip Capacity Test described in detail in European patent application no. 93309614.1

Suitable first fibrous material can comprise chemically stiffened cellulosic fibres, generally in an amount of 50 to 100% by weight of the first fibrous material and 0 to 50% by weight other fibres such as non-stiffened cellulose fibres and synthetic fibres. Preferred chemically stiffened cellulosic fibres are stiffened, twisted, curled cellulosic fibres which can be produced by internally cross-linking cellulose fibres with a cross-linking agent. The types of stiffened, twisted, curled cellulosic fibres useful as the hydrophilic fibre material of the absorbent structures described herein are described in greater detail in the following patents: U.S. Pat. No. 4,822,453 entitled "Absorbent Structure Containing Individualised Cross-linked Fibres", issued to Dean et al. on Apr. 18, 1989; U.S. Pat. No. 4,888,093 entitled "Individualised, Cross-linked Fibres And Process For Making Said Fibres", issued to Dean et al. on Dec. 19, 1989; U.S. Pat. No. 4,889,595 entitled "Process For Making Individualised, Cross-linked Fibres Having Reduced Residuals And Fibres Thereof", issued to Herron et al. on Dec. 26, 1989; U.S. Pat. No. 4,889,596 entitled "Process for Making Individualised Cross-linked Fibres and Thereof", issued to Schoggen et al. on Dec. 26, 1989; U.S. Pat. No. 4,889,597 entitled "Process For Making Wet-Laid Structures Containing Individualised Stiffened Fibres", issued to Bourbon et al. on Dec. 26, 1989; and U.S. Pat. No. 4,898,642 entitled "Twisted, Chemically Stiffened Cellulosic Fibres And Absorbent Structures Made Therefrom", issued to Moore et al. on Feb. 5, 1990.

Instead of using stiffened cellulosic fibres, it is also possible to formulate the layer from synthetic polymer fibres, or mixtures of synthetic and natural fibres. Suitable fibres are polyethylene, polypropylene, viscose and rayon fibres, and bi-component fibres of these materials, mixed with airfelt, cellulose, modified cellulose (as above) or other natural fibres. Typically such a mixture will have at least about 5% synthetic fibres, and preferably at least about 10% synthetic fibres.

The first fibrous material layer is generally formed by air laying the desired fibres during or prior to the production of the absorbent core, but if desired a preformed non-woven or a wet or air laid or other fibrous material can be used. The layer 36 may also be completely or partly formed by an absorbent foam material.

The hydrogel-forming layer 34 consisting mainly of first hydrogel-forming material may be crosslinked to the lower part of the acquisition layer 36, but preferably is attached to a tissue layer, which tissue layer may be a separate layer, or may preferably be formed by layer 39.

It is important that this layer 34 consisting mainly of first hydrogel-forming material should allow urine, menstrual fluids or other body discharges that are rapidly acquired by and distributed by the first fibrous layer to pass rapidly through and be distributed beyond the layer of first hydrogel-forming material without significant blockage by that layer.

The amount of the first hydrogel-forming material should be sufficient to provide at least a substantially overall layer of hydrogel-forming material when swollen by absorption of urine in use, but a window as shown in FIG. 6 may be provided. The hydrogel-forming material is usually in particulate form and it is usually necessary for it to be present in an amount of at least about 20 g/m$^2$. Generally the layer should not be too thick and normally the amount is below 100 g/m$^2$.

Lower Assembly

The lower layers 37, 39 serve as a storage and redistribution assembly and includes an upper, usually fibrous, layer 39 and a layer of second hydrogel-forming material 37.

The upper layer 39 in the lower assembly is generally fibrous but can be formed of foam or other suitable capillary or porous material. It provides void space for storage of liquid. The fibrous or other material of this layer can add an extra stage of control to the absorption profile of the absorbent body of the invention. For instance it may slow down the passage of body discharges as they leave the first hydrogel-forming layer and prior to them reaching the second hydrogel-forming layer material. This may minimise the chances of gel-blocking occurring in the second hydrogel-forming material, and this can be particularly useful in those embodiments where the second hydrogel-forming material has faster absorption kinetics and so tends to be more sensitive to this phenomenon.

The second fibrous material of layer 39 may comprise fibrous material of any conventional type. The fibrous material can be airfelt, a mixture of natural and synthetic fibres, chemically cross-linked cellulose fibre or any other known fibrous material commonly used in absorbent cores of absorbent articles. If desired it may include some fibres of the same type as the first fibrous material. The layer 39 may also be completely or partly formed by an absorbent foam material.

Each fibrous layer may add integrity and may also add softness to the absorbent core.

The layer 39 may be substantially or wholly free of hydrogel-forming material and thus may be an air felt or other fibrous or storage layer formed in the absence of hydrogel-forming material. The lower layer can then be a separately formed layer comprising second hydrogel-forming material. The layer 39 may be a blend with fibres or may consist mainly of the hydrogel-forming material. As shown in FIG. 8 the layer 37 may ba comprised of an interparticle cross-linked aggregate as described in U.S. Pat. No. 5,102,597 (Roe) or U.S. application Ser. No. 08/142,258 (Hsueh).

However it is often desirable for the layers 37, 39 to be formed as in EP-A-198 683 (Duenk), wherein the layers are provided by a continuous air laid fibrous matrix wherein more than half by weight, and usually at least 70% by weight, of the hydrogel-forming material is comprised in the lower half of the thickness of the fibrous matrix. In this case for instance 70 to 100%, often 70 or 75 to 90 or 95% by weight of the second hydrogel-forming material is in the lower 50% of the thickness of the fibrous matrix. There can be some, for instance 5% to 10% or sometimes up to 30%, of the second hydrogel-forming material in the upper half of the thickness of the fibrous matrix as described in EP-A-198 683.

Generally the layers 37, 39 are provided by air laying a blend of appropriate wood pulp or other hydrophilic fibres for instance on to a conventional air laying drum or other receiving surface. The distribution of hydrogel-forming material through the thickness of layers 37, 39 can be achieved by appropriate selection of the distribution of hydrogel-forming material into the stream of fibers being carried down on to the receiving surface, for instance as described in EP-A-198 683, or by injecting or otherwise distributing the hydrogel-forming particles the air laid matrix as it is formed on the receiving surface.

When air laying such a matrix, it is generally desirable additionally to provide a fiber layer 38 substantially free of hydrogel-forming material which is air laid with and beneath the layer 37.

Instead of or in addition to this a layer 38 of separately formed tissue or other fibrous material may be provided in this position.

Typically the amount of second hydrogel-forming material is 30 to 95%, preferably 45 to 75%, by weight of the upper and lower layers 37, 39. Its total basis weight is typically in the range 100 to 2000 g/m$^2$.

Superabsorbent Materials

One suitable definition of first hydrogel-forming material which can be included in useful amounts in that layer is the Gel Layer Permeability value (GLP) measured by the GLP test described in European patent application no. 93309614.1. The first hydrogel-forming material in layer 34 should generally have a GLP value of at least 6, preferably at least 9, for instance more than 15 and up to 150×10$^{-7}$ cm$^3$ s/g or more.

The objective of the Gel Layer Permeability (GLP) test is to determine the saline flow conductivity of the gel layer formed from a dispersible Hydrogel-forming particles that is swollen in Jayco synthetic urine under a confining pressure. The flow conductivity provides a measure of the ability of the gel layer formed from a swollen Hydrogel-forming particles to acquire and distribute fluid during use in an absorbent structure. Darcy's law and steady-state flow methods are used for measuring gel-layer permeability and determining saline flow conductivity. (See, for example, "Absorbency", ed. by P. K. Chatterjee, Elsevier, 1985, Pages 42–43 and "Chemical Engineering Vol. II, Third Edition, J. M. Coulson and J. F. Richardson, Pergamon Press, 1978, Pages 125–127.)

The gel layer used for permeability measurements is formed by swelling Hydrogel-forming particles in Jayco synthetic urine for a time period of 60 minutes. The gel layer is formed and its flow conductivity measured in a piston/cylinder apparatus under a mechanical confining pressure of 0.3 psi. The bottom of the cylinder is faced with a No 400 mesh screen to retain dry-swollen Hydrogel-forming particles and permit absorption and z-direction transport of urine. The piston is permeable to fluid. Flow conductivity is measured using a 0.118M NaCl solution. For an Hydrogel-forming particles whose uptake of Jayco synthetic urine versus time has substantially levelled off, this concentration of NaCl has been found to maintain the thickness of the gel layer substantially constant during the permeability measurement. For some Hydrogel-forming particles, small changes in gel-layer thickness can occur as a result of Hydrogel-forming particles swelling, Hydrogel-forming particles deswelling, and/or changes in gel-layer porosity. A constant hydrostatic pressure of 4920 dyne/cm$^2$ (5 cm of 0.118M NaCl), above the gel layer, is used for the measurement.

Flow rate is determined by measuring the quantity of solution flowing through the gel layer as a function of time. Flow rate may vary over the duration of the experiment. Reasons for flow-rate variation include changes in the thickness of the gel layer and changes in the viscosity of interstitial fluid, as the fluid initially present in interstitial voids (which, for example, can contain dissolved extractable polymer) is replaced with NaCl solution. If flow rate is time dependent, then the initial flow rate, typically obtained by extrapolating the measured flow rates to zero time, is used to calculate flow conductivity. The saline flow conductivity is calculated from the initial flow rate, dimensions of the gel bed, and hydrostatic pressure. For systems where the flow rate is substantially constant, a gel-layer permeability coefficient can be calculated from the saline flow conductivity and the viscosity of the NaCl solution.

Another way of defining useful materials is in terms of the Dynamic Swelling Rate. Suitable materials have a substantially non-decreasing Dynamic Swelling Rate.

The Dynamic Swelling Rate of a hydrogel-forming material is a measure of the uniaxial swelling of the hydrogel-forming material in a test tube as synthetic urine is added to it as a function of time. The test method used to measure the dynamic swelling rate is called the Dynamic Swelling Rate Test, and is described European patent application no. 93309614.1. By saying that the Swelling Rate is substantially is substantially non-decreasing, it is meant that the relative deviation of the Swelling Rates should be less than 50%, preferably less than 25%, more preferably less than 10% and most preferably less than or equal to zero percent.

The first hydrogel-forming material in layer 34 generally has Absorption Against Pressure value of at least 15, and generally at least 20, g/g at 50 g/cm$^2$. The Performance Under Pressure value is generally more than 20 g/g and preferably more than 30 g/g. Methods for measuring the Performance Under Pressure values and Absorption Against Pressure values have been described in European application no. 93309614.1

The hydrogel-forming material in layer 37 should have an Absorption Against Pressure of at least 15, and preferably at least 20, g/g at 50 g/cm² (0.7 psi) pressure, The Performance Under Pressure value is generally more than 20 g/g and preferably more than 30 g/g.

Useful results can be obtained when the same material is used in the layers 34 and 37, in which event the first hydrogel-forming material 34 will have the same Absorption Against Pressure value as the second material in lower layer 37. However different materials can be used and in order to optimise performance in some respects, and in particular to obtain greater control in the flow and absorption of urine and other fluid discharges within the core, it can be preferred for the hydrogel-forming material in layer 37 to have absorption kinetics which are faster than those of the material in the first layer 34. This is measured in terms of the Dynamic Swelling Rate of each of the hydrogel-forming materials, wherein the dynamic swelling rate of the first hydrogel-forming material in layer 34 is preferably not greater than ⅔, and preferably not greater than ⅓, of that of the hydrogel-forming material in layer 37. The alternative way of defining this difference is to say that the Dynamic Swelling Rate of the hydrogel-forming material in the lower layer 37 is preferably at least 1.5 times, and most preferably at least 3 times, the Dynamic Swelling Rate of the first hydrogel-forming material upper layer 34.

It is desirable, especially when the hydrogel-forming material in layer 37 has faster absorption kinetics, for it to have a Dynamic Swelling Rate of at least 0.2 grams urine per second per gram of hydrogel-forming material (g $g^{-1}$ $s^{-1}$). Preferably the Dynamic Swelling Rate of the hydrogel-forming material in layer 37 is at least 0.3 g $g^{-1}$ $s^{-1}$ and it can be up to, for instance, 0.6 or even 1 g/g/s.

The hydrogel-forming materials in layers 34,37 may be of any suitable physical shape, e.g. fibrous or particulate. Preferred materials are particles that may be true spheres, granules, aggregates, agglomerates or irregular shaped particles as typically produced by a grinding process.

An example of hydrogel-forming materials having the above described properties is Favor SX (available from Chemische Fabrik Stockhausen GmbH, Krefeld, Germany). In particular, it is desirable to use as the hydrogel-forming material in layer 34 Favor SX, Type P, lot no W51776 available from Chemische Fabrik Stockhausen which have a GLP value of $9 \times 10^{-7}$ cm³ sec/g.

In one embodiment, the hydrogel-forming materials in the layers 34,37 have different absorption kinetics, and in particular the hydrogel-forming material in layer 37 has faster absorption kinetics than the hydrogel-forming material in upper layer 34, for instance having a Dynamic Swelling Rate of at least 0.2 g $g^{-1}$ $s^{-1}$ and/or a Dynamic Swelling Rate that is preferably at least 1.5 times, and most preferably at least 3 times, the Dynamic Swelling Rate of the upper hydrogel-forming material. The provision of this underlying, rapidly absorbing, hydrogel-forming material in lower layer 37 will have the effect of tending to "suck" urine through the upper assembly into the lower assembly.

Pantiliner

The composite absorbent structure as shown in FIGS. 2 and 3, comprising a single tissue and a single layer of hydrogel-forming particles 2, is especially suitable for use as the absorbent core of a pantiliner. Pantiliners are to be used in between menstrual periods, and generally have a relatively low total absorbent capacity, such as between 5 and 20 ml grams. The amounts of hydrogel-forming particles in a typical pantiliner ranges between 10 and 50 g/sqm. A pantiliner generally consist of a topsheet, an liquid impervious backsheet and an absorbent core encased between topsheet and backsheet. As the amounts of liquid that are to be absorbed by a pantiliner are relatively low, the impermeable backsheet can optionally be omitted. A layer of panti-fastening adhesive, applied to the garment-facing side of the pantiliner, provides in that case additional fluid containment. A detailed description of a pantiliner is given in U.S. Pat. No. 4,681,578.

Thin, Flexible Sanitary Napkin

Figure 9:
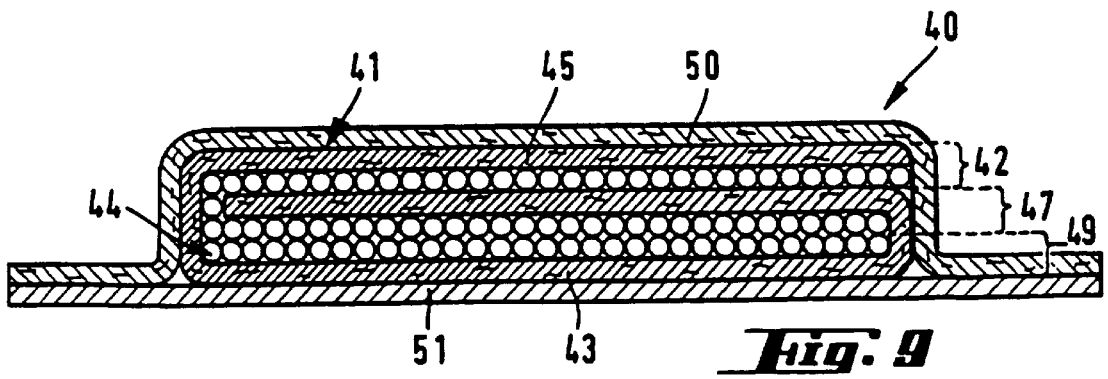
FIG. 9 shows a cross-sectional view of a thin, flexible sanitary napkin comprising an absorbent core formed form an absorbent composite structure according to invention.

The composite absorbent structures as shown in FIGS. 2 to 6 and the multi-layer cores as shown in FIGS. 7 and 8 are suitable for forming the core of a thin, flexible sanitary napkin 40 as shown in FIG. 9 and as described in U.S. Pat. No. 4,950,264. A thin, flexible sanitary napkin 40 has a test capacity which is at least 8 g of saline solution, and a total capacity of at least 20 g of saline solution. The test capacity is measured by submerging a part of the sanitary napkin having a surface area of 66.5 cm² in a saline solution, and measuring how many grams of liquid are retained after desorption against blotter paper. The method for measuring the test capacity is described in detail in Column 13, line 44 to Column 14 line 33 of U.S. Pat. No. 4,950,264. The total capacity is measured in the same manner as the test capacity, using the total sanitary napkin instead of a cut-out portion.

The absorbent core 41 in FIG. 9 is formed by folding of an absorbent composite structure as shown in FIG. 3. This folding process can results in a multilayer core of the type as shown in FIG. 9 wherein the top layer 42 of hydrogel-forming particles is a single layer and wherein the bottom layer 44 comprises two layers of hydrogel-forming particles. Furthermore, hydrogel-forming particles of specific physical properties can be applied to the area 45 of the unfolded substrate 43 that corresponds to the top layer 42 and which comprises about ⅓ of the width of the substrate. To the area corresponding to the unfolded lower layers 47,49 of the substrate 43, which comprises about ⅔ of the width of substrate, hydrogel-forming particles of different type can be applied, such that for instance the GLP-values as described above are obtained.

Alternatively the core of the sanitary napkin comprises an unfolded structure as shown in FIG. 3.

A thin, flexible sanitary napkins generally comprise a basis weight of hydrogel-forming particles of about 50 g/m². Higher basis weights may be obtained by stacking of a number of absorbent composite structures as shown in FIG. 3, or by folding of a single composite structure. The sanitary napkin 40 can comprise a wet laid tissue superimposed on the core 41, a topsheet 50 in the form of an apertured formed plastic film, and a flexible polyethylene backsheet 51 of caliper between 12 and 51 micrometers. The total caliper of the sanitary napkin 40 is less than 5 mm, preferably less than 3 mm.

The composite absorbent structures according to the invention are especially useful in a thin sanitary napkin of the above kind, as the flexibility of the absorbent composite structures according to the invention is high and allows formation of sanitary napkins having a flexure resistance of less than 300 grams.

The flexure resistance is measured by the peak bending stiffness in a modified ASTM D 4032-82 Circular Bend Procedure, in which deformation of the material under test takes place in a way that one face of the material becomes convex, the other face becoming concave. The modified Circular Bend Procedure gives a force value related to flexure-resistance, simultaneously averaging stiffness in all direction. The above procedure is described in detail in U.S. Pat. No. 4,950,264 on Column 10 line 55 to Column 12 line 16.

Alternatively, the flexibility of absorbent structures can be expressed in gramforce.cm as measured in a bending test as set out below.

Figure 10:
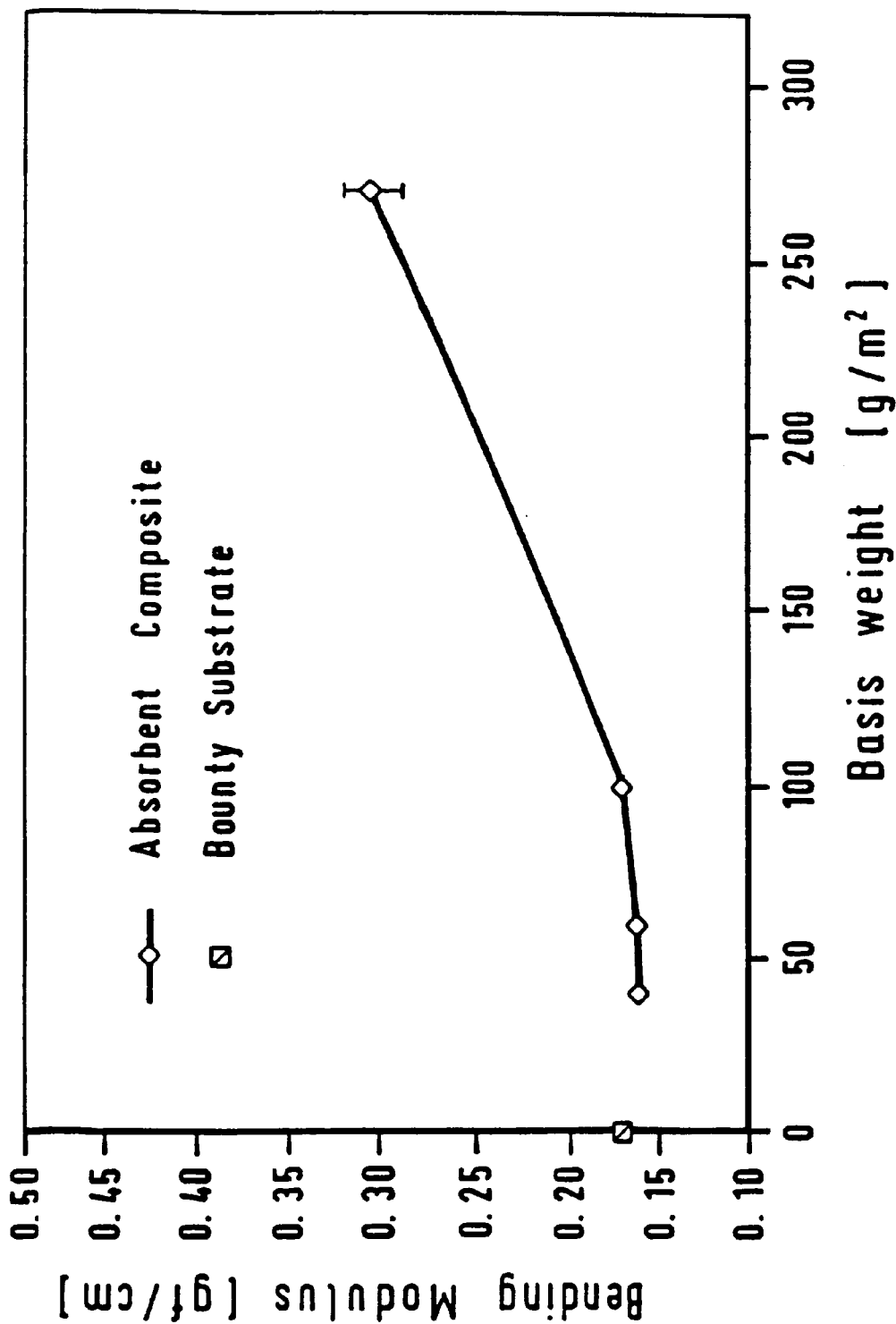
FIG. 10 shows the flexibility of an absorbent composite structure according to the invention, for varying basis weight of hydrogel-forming particles

In the following test, the flexibility of an absorbent composite structure comprising a substrate and varying basis weights of hydrogel-forming material is measured. The results are graphically depicted in FIG. 10. The hydrogel-forming material used in the present test is produced by Nippon Shokubai Co. under the trade name Acqualic L76lf, which was bonded to the substrate by application of a solution comprising 10% by weight of Kymene® 557 Plus, 40% by weight of glycerol and 50% by weight of water.

In the test a 1 inch×3 inch sample is placed into a PURE BENDING TESTER, with serial number KES-FB2, made by KATO Tech. Co., LTD.: Nihonseimie Kyoto Santetsu Bldg. 3F, 608-9 Higashishiokoji-cho, Shiokoji Agaru, Nishi-notoindohri Shimogyo-ku, Kyoto, Japan. The sample is bent by 180°, returned to its original position, and is then bent in the opposite direction by 180°. The force needed to bend the sample and the relaxation of the sample are measured by a computer and are recorded for a total of four bends in each direction. The average slope of the hysteresis curve in the first and third quadrants is recorded. The bending modulus of the sample corresponds to the slope of the hysteresis curve and is expressed in gramforce.cm$^2$/cm. During the test the air humidity was 50% and the temperature 73° F.

The substrate of the absorbent composite structure is a Bounty® tissue produced by The Procter & Gamble Company.

The flexibility of the Bounty® substrate tissue was 0.17 gramforce.cm$^2$/cm. From FIG. 10 it can be seen that the flexibility of the absorbent composite structure remains close to the flexibility of the substrate tissue for basis weights up to about 100 g cm$^{-2}$, and increases for higher basis weights. An explanation for this is that for higher basis weights, the hydrogel-forming particles become attached to one another by interparticle crosslinked bonds such that macroscopic interparticle crosslinked aggregates are formed.

Further Embodiments

Figure 11:
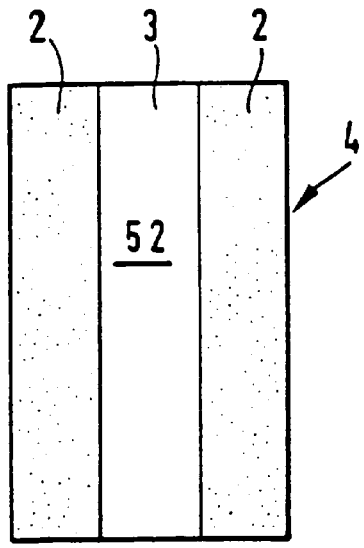
FIGS. 11–14 show plan views of embodiments of different patterns of hydrogel-forming particles attached to a substrate.
Figure 12:
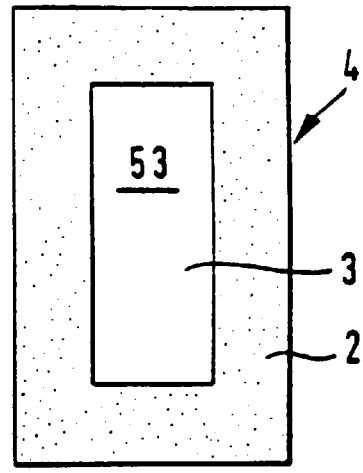
Figure 13:
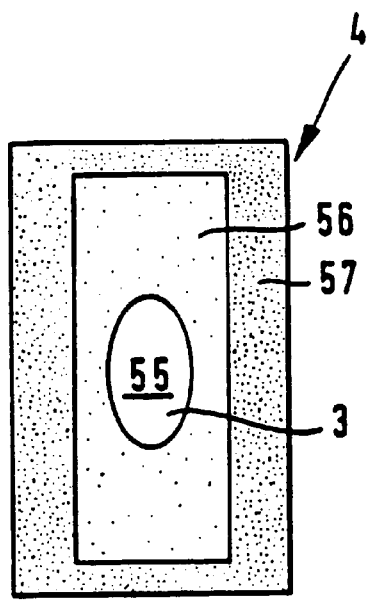
Figure 14:
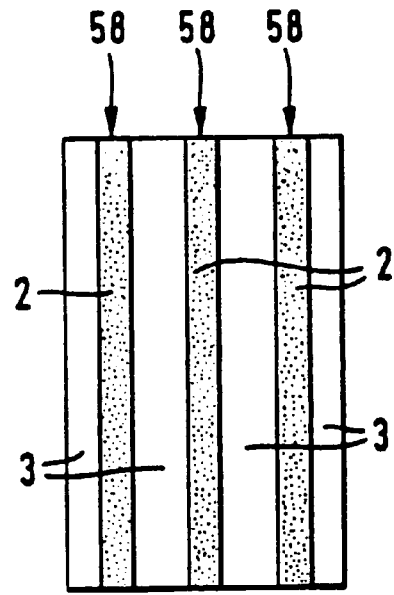

FIGS. 11 to 14 show a top view of a composite absorbent structure 4 in which the hydrogel-forming particles are applied onto the substrate 3 in patterns of varying basis weights. In FIG. 11 a central longitudinal channel 52 is formed for promoting liquid transport in the longitudinal direction. In FIG. 12 a central window 53 is formed for receiving gushes of liquids, while maintaining absorption in the peripheral areas of the composite structure. In FIG. 13, the concentration of hydrogel-forming particles increases from the central area 55 of the absorbent structure to the middle area 56 and the side margin 57. In FIG. 14, a number of parallel stripes 58 of hydrogel-forming particles are formed by which longitudinal liquid flow is promoted. These structures can be formed by applying a crosslinking agent only to selected areas of the substrate or by varying the amount of the crosslinking agent applied, and uniformly distributing the hydrogel forming particles onto the substrate. The areas in which no hydrogel-forming particles are to be bonded to the substrate can for instance be shielded by using a mask between the spray nozzle and the substrate. This is described in detail in co-pending European application no. (attorney docket ROI 833), filed by the Applicant. Alternatively, a crosslinking agent can be homogeneously applied, the hydrogel-forming particles being laid down on the substrate in a pattern of varying basis weight.

Figure 15:
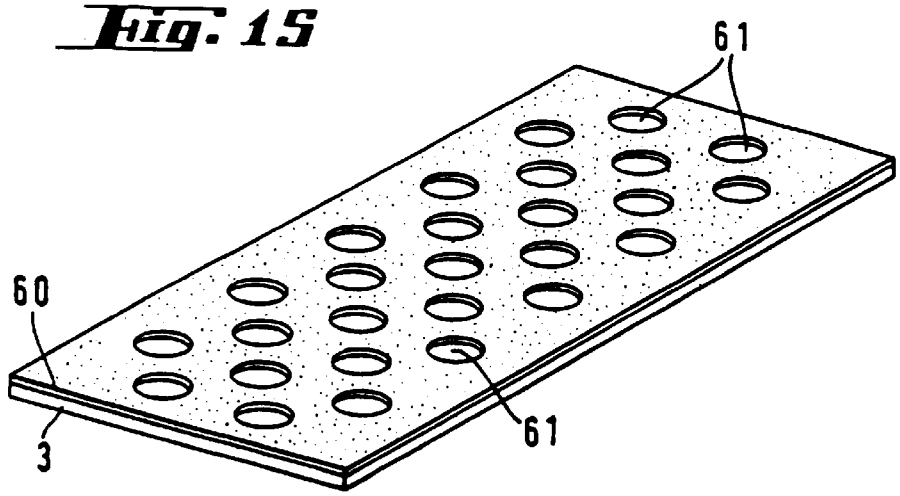
FIG. 15 shows a perspective view of a composite absorbent structure having holes in the layer of hydrogel-forming particles.
Figure 16:
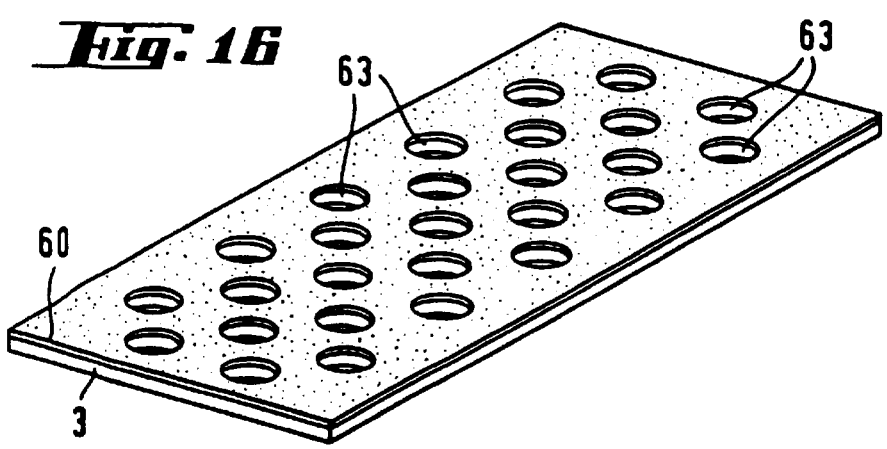
FIG. 16 shows a perspective view of a composite absorbent structure having holes in both the layer of hydrogel forming particles and the substrate.

FIG. 15 shows a perspective view of an embodiment in which a pattern of holes 61 is left open in the layer 60 of hydrogel-forming particles that covers the substrate 3. In the embodiment of FIG. 16, holes 63 have been cut through the hydrogel-forming layer 60 and the substrate 3 to provide further flexibility and to improve liquid transmissive properties of the composite absorbent structure.

Figure 17:
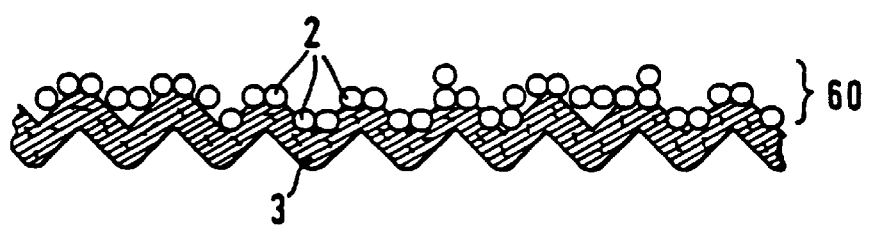
FIG. 17 shows a cross-sectional view of an extensible composite absorbent structure having a plurality of corrugations.

In FIG. 17, an alternative embodiment is shown in which extensibility is imparted to the substrate 3 by passing it through intermeshing corrugated members, also referred to as "ringrolling", as described in detail in international patent application WO 92/15445 and in U.S. Pat. Nos. 5,156,793 and 5,143,679. The advantage of the composite absorbent structure according to the invention is that the upper layer 60 of hydrogel-forming particles 2 is not substantially damaged by the ringrolling process, and that due to the strong crosslink bonds between each particle 2 and the substrate 3, these particle do not easily detach from the substrate.

Figure 18:
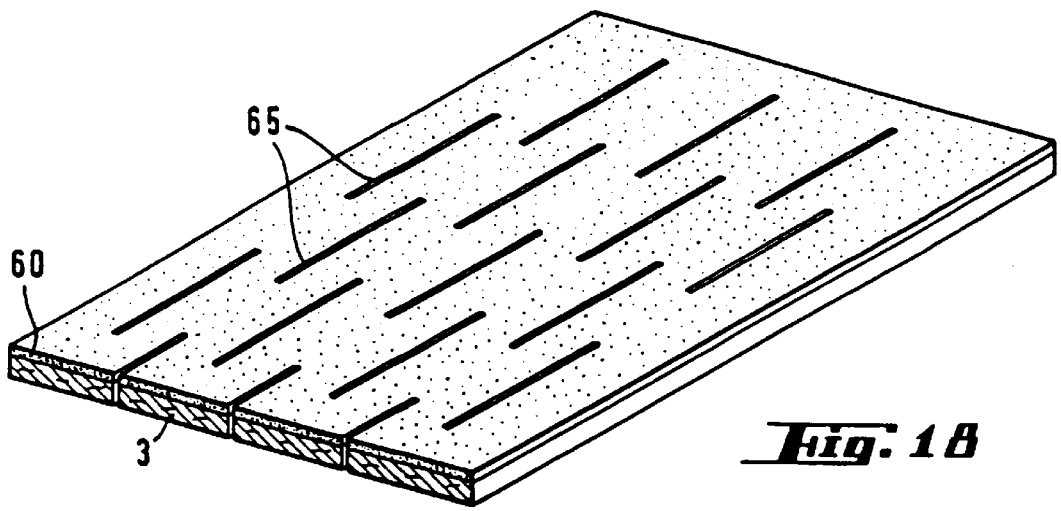
FIG. 18 shows a perspective view of a composite absorbent structure that is slitted.

In the embodiment of FIG. 18 a number of longitudinal slits 65 is formed in the substrate, which impart improved extensibility and flexibility to the substrate in the direction transverse to the slits.

Slitting of absorbent cellulosic foam structures to impart improved flexibility has been described in EP-A-0 293 208. This technology can be applied to the composite absorbent structures according to the present invention.

In a further embodiment, the absorbent structure according to the invention is elastically extensible, for instance due to elastic properties of the substrate or due to separate elastication of the substrate by combining with elastic members. Elastic absorbent structures have been described in detail in EP-A-0 552 345.

Figure 19:
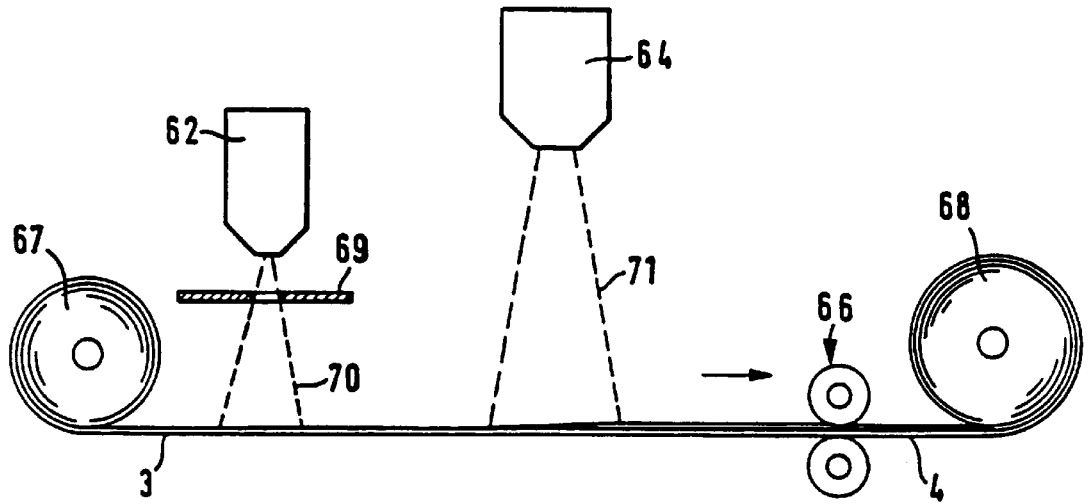
FIG. 19 shows a schematic view of an apparatus for forming composite absorbent structures according to the invention.

FIG. 19 schematically shows a method of manufacturing a composite absorbent article according to the invention. A substrate 3 is unwound from a supply roll 67 and passed underneath a nozzle 62. Cross-linking agent 70 is sprayed onto the substrate, either homogeneously or in a pattern. Patterns of cross-linking agent may be obtained by shielding certain areas of the substrate 3 by a mask 69 placed between the nozzle 62 and the substrate 3. From a dispenser 64 a stream 71 of hydrogel-forming particles is deposited onto the substrate in basis weights below 100 gm$^{-2}$. In a nip 66, the substrate 3 and particles are bonded by curing of the cross-linking agent under increased temperature and pressure conditions. It is also possible that the nip 66 is omitted if a crosslinking agent is used which cures at room temperature and pressure. Finally, the finished absorbent composite structure 4 is wound on a storage roll 68.

Further methods of manufacturing an absorbent composite structure are disclosed in copending European patent application (attorney docket ROI 833).

We claim:

1. An absorbent composite structure suitable for absorbing aqueous body fluids comprising:

a substrate having two surfaces;

a plurality of hydrogel-forming polymer particles; and a chemical cross-linking agent capable of bonding to both said substrate and said hydrogel-forming particles;

wherein, in at least a substantial portion of said structure, the majority of said particles in said portion are connected by said chemical cross-linking agent directly to at least one of said substrate surfaces.

2. The absorbent composite structure of claim 1 wherein the degree of any connection between adjacent hydrogel-forming particles by said cross-linking agent in said portion is sufficiently low that substantially no interparticle macrostructures having a circumscribed dry volume larger than 10 $mm^3$ are present in said portion.

3. The absorbent composite structure of claim 1 wherein substantially each said hydrogel-forming particle in said portion of said structure is connected by said chemical cross-linking agent directly to at least one of said substrate surfaces.

4. The absorbent composite structure of claim 1 wherein said substrate comprises a material selected from the group consisting of cellulose and polyvinyl alcohol.

5. The absorbent composite structure of claim 1 wherein said chemical cross-linking agent is a cationic amino-epichlorohydrin adduct.

6. The absorbent composite structure of claim 5 wherein said hydrogel-forming particles comprise an anionic functional group.

7. The absorbent composite structure of claim 1 wherein said hydrogel-forming particles are connected to both surfaces of said substrate, a first amount of said hydrogel-forming particles being connected to one of said surfaces and the remaining amount of said hydrogel-forming particles being connected to the other of said surfaces.

8. The absorbent composite structure of claim 1 wherein said substrate has at least two areas to which said hydrogel-forming particles are connected, the respective basis weights of the hydrogel-forming particles connected to said two areas being different.

9. The absorbent composite structure of claim 1 wherein said substrate comprises at least two areas to which hydrogel-forming particles having different chemical or physical properties are respectively connected.

10. The absorbent composite structure of claim 1 wherein the basis weight of said hydrogel-forming particles in said portion of said structure is not higher than 100 $g/m^2$.

11. The absorbent composite structure of claim 1 wherein said substrate comprises a foamed or fibrous absorbent material.

12. The absorbent composite structure of claim 1 comprising a second substrate, said hydrogel-forming particles being located between said substrate and said second substrate.

13. The absorbent composite structure of claim 8, wherein said two areas are respectively on opposite surfaces of said substrate.

14. The absorbent composite structure of claim 1 wherein said substrate is extensible by at least 5 percent.

15. The absorbent composite structure of claim 14 wherein said substrate is elastically extensible.

16. An absorbent article comprising the absorbent composite structure of claim 1.

17. The absorbent article of claim 16, said article comprising a liquid pervious topsheet and a liquid impervious backsheet, said absorbent composite structure being located between said topsheet and said backsheet, and said absorbent article having a flexure resistance of less than 300 grams.

18. An absorbent article comprising an absorbent core having a body-facing upper face, wherein said absorbent core comprises from the upper face downward:

an upper acquisition layer, the absorbent composite structure of claim 1; and a lower layer comprising an absorbent gelling material.

19. The absorbent composite structure of claim 1 wherein said substrate is extensible by at least 10 percent.

20. The absorbent article of claim 17 wherein the thickness of said article is less than 5 millimeters.

21. A method of making a composite absorbent structure suitable for absorbing aqueous bodyfluids, the method comprising the steps of:

providing a substrate;

providing a plurality of organic hydrogel-forming polymer particles;

applying to said substrate a chemical cross-linking agent capable of chemically bonding with both said hydrogel-forming particles and said substrate; and applying said hydrogel-forming particles to said substrate such that, in at least a substantial portion of said structure, the majority of said particles in said portion are directly connected to said substrate by said chemical cross-linking agent.

22. The method of claim 21 wherein the degree of any connection between adjacent hydrogel-forming particles by said chemical cross-linking agent in said portion is kept sufficiently low such that substantially no interparticle macrostructures having a circumscribed dry volume larger than 10 $mm^3$ are formed in said portion.

23. The method of claim 1 wherein said method further comprises the step of compressing said absorbent composite structure after application of said particles to said substrate.

* * * * *

UNITED STATES PATENT AND TRADEMARK OFFICE
CERTIFICATE OF CORRECTION

PATENT NO.   : 5,977,014
DATED        : November 2, 1999
INVENTOR(S)  : Plischke et al.

It is certified that error appears in the above-identified patent and that said Letters Patent is hereby corrected as shown below:

Column 2,
Line 13, please delete "at" and insert therefor -- et --.

Column 4,
Line 62, please delete "93309514.1" and insert therefor -- 93309614.1 --.

Column 6,
Line 48, after "inter-particle" please delete "is".

Column 9,
Line 1, please delete "nitrate" and insert therefor -- nitrile --.
Line 47, please delete "acrylatelacrylic" and insert therefor -- acrylate/acrylic --.

Column 17,
Line 31, please delete "Go." and insert therefor -- Co. --.
Line 48, please delete "determin ed" and insert therefor -- determined --.

Column 21,
Line 17, please delete "35" and insert therefor -- 36 --.

Column 23,
Line 17, please delete "ba" and insert therefor -- be --.

Column 24,
Line 41, please delete "NaCI" and insert therefor -- NaCl --.

Column 28,
Line 2, please delete "hydrogel forming" and insert therefor -- hydrogel-forming --.

UNITED STATES PATENT AND TRADEMARK OFFICE
CERTIFICATE OF CORRECTION

PATENT NO. : 5,977,014
DATED : November 2, 1999
INVENTOR(S) : Plischke et al.

It is certified that error appears in the above-identified patent and that said Letters Patent is hereby corrected as shown below:

Column 30,
Line 29, please delete "bodyfluids" and insert therefor -- body fluids --.
Line 47, please delete "1" and insert therefor -- 21 --.

Signed and Sealed this

Eighteenth Day of February, 2003

JAMES E. ROGAN
*Director of the United States Patent and Trademark Office*